US012733841B2

(12) United States Patent
Meng et al.

(10) Patent No.: US 12,733,841 B2
(45) Date of Patent: Sep. 15, 2026

(54) HUMAN MOVEMENT INTELLIGENT MEASUREMENT AND DIGITAL TRAINING SYSTEM

(71) Applicant: BEIJING AEROSPACE TIMES OPTICAL ELECTRONIC TECHNOLOGY CO LTD, Beijing (CN)

(72) Inventors: XiangTao Meng, Beijing (CN); Zheng Xiang, Beijing (CN); JiLin Wang, Beijing (CN); HongSheng Ge, Beijing (CN)

(73) Assignee: BEIJING AEROSPACE TIMES OPTICAL ELECTRONIC TECHNOLOGY CO LTD, Beijing (CN)

( * ) Notice: Subject to any disclaimer, the term of this patent is extended or adjusted under 35 U.S.C. 154(b) by 301 days.

(21) Appl. No.: 18/578,620

(22) PCT Filed: Dec. 29, 2022

(86) PCT No.: PCT/CN2022/143225
§ 371 (c)(1),
(2) Date: Jan. 11, 2024

(87) PCT Pub. No.: WO2023/221524
PCT Pub. Date: Nov. 23, 2023

(65) Prior Publication Data

US 2024/0306943 A1 Sep. 19, 2024

(30) Foreign Application Priority Data

May 20, 2022 (CN) ......................... 202210555949.2

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/1116* (2013.01); *A61B 5/6802* (2013.01);
(Continued)

(58) Field of Classification Search
CPC ... A61B 5/1128; A61B 5/1116; A61B 5/6802; A61B 5/11; A63B 24/0003;
(Continued)

(56) References Cited

U.S. PATENT DOCUMENTS 6,710,713 B1 3/2004 Russo
2006/0161363 A1 7/2006 Shibasaki et al.
(Continued)

FOREIGN PATENT DOCUMENTS

CN 102323854 A 1/2012
CN 108939512 A 12/2018
(Continued)

OTHER PUBLICATIONS

CN Office Action, including Search Report Mailed on Mar. 7, 2023 for CN Application No. 202210555949, 10 page(s).
(Continued)

*Primary Examiner* — Sean P Dougherty
(74) *Attorney, Agent, or Firm* — Workman Nydegger

(57) ABSTRACT

Provided is a human movement intelligent measurement and digital training system, which comprises N inertial navigation wearable devices, M cameras, a data comprehensive analysis device, and a terminal. The total view field of the M cameras covers the whole movement scenario of an athlete; the inertial navigation wearable devices are fixed on limbs of the athlete in a wearable manner and measure to obtain a three-axis acceleration of the limbs of the athlete and a three-axis angular velocity under an inertial coordinate system; the data comprehensive analysis device determines movement parameters of each athlete; the terminal estab-
(Continued)

lishes a movement scenario and a three-dimensional model of the athlete and displays the movement process and the movement parameters of the athlete in a visual mode

19 Claims, 5 Drawing Sheets

(51) Int. Cl.

| | |
|---|---|
| ***A63B 24/00*** | (2006.01) |
| ***G01C 21/16*** | (2006.01) |
| ***G06T 7/20*** | (2017.01) |
| ***G06T 7/70*** | (2017.01) |

(52) U.S. Cl.
CPC ....... *A61B 2505/09* (2013.01); *A63B 24/0003* (2013.01); *A63B 24/0021* (2013.01); *A63B 24/0062* (2013.01); *G01C 21/16* (2013.01); *G06T 7/20* (2013.01); *G06T 7/70* (2017.01)

(58) Field of Classification Search
CPC ...... A63B 24/0062; G01C 21/16; G06T 7/20; G06T 7/70
See application file for complete search history.

(56) References Cited

U.S. PATENT DOCUMENTS

| | | | | |
|---|---|---|---|---|
| 2017/0136296 | A1 | 5/2017 | Barrera | |
| 2017/0259115 | A1* | 9/2017 | Hall | G16H 40/67 |
| 2018/0070863 | A1 | 3/2018 | Matsumura et al. | |
| 2018/0089841 | A1* | 3/2018 | Dai | G01P 3/38 |
| 2019/0273909 | A1* | 9/2019 | Ye | G06T 7/579 |
| 2020/0302645 | A1* | 9/2020 | Parchami | G06N 3/0464 |
| 2020/0348138 | A1* | 11/2020 | Le | G06T 7/20 |
| 2022/0001236 | A1 | 1/2022 | Mooney | |

FOREIGN PATENT DOCUMENTS

| | | | |
|---|---|---|---|
| CN | 109284006 | A | 1/2019 |
| CN | 110095116 | A | 8/2019 |
| CN | 110393533 | A | 11/2019 |
| CN | 111693024 | A | 9/2020 |
| CN | 112706158 | A | 4/2021 |
| CN | 113793360 | A | 12/2021 |
| CN | 114191797 | A | 3/2022 |
| CN | 115024715 | A | 9/2022 |
| JP | 2018-207475 | A | 12/2018 |
| JP | 2019-144622 | A | 8/2019 |
| KR | 10-2018-0062068 | A | 6/2018 |
| KR | 10-2021-0020499 | A | 2/2021 |
| WO | 2016/194330 | A1 | 12/2016 |
| WO | 2020/074596 | A1 | 4/2020 |
| WO | 2020/087846 | A1 | 5/2020 |

OTHER PUBLICATIONS

International Search Report and Written Opinion received for PCT Patent Application No. PCT/CN2022/143225, mailed on Mar. 9, 2023, 14 pages (3 pages of English Translation and 11 pages of Original Document).

JP Office Action Mailed on Aug. 26, 2024 for JP Application No. 2023571673, 13 page(s).

Yu et al., Based on Mahony algorithm swimming luck moving gesture fast measurement quick alignment, vol. 20, Jun. 30, 2021, pp. 17-24.

Yu et al., Indoor positioning technology is used in swimming luck feasibility analysis of dynamic measurement, vol. 649, No. 6, pp. 171-173.

International Search Report for International Application No. PCT/CN2022/143225, mailed Mar. 9, 2023, 12 pages.

* cited by examiner

HUMAN MOVEMENT INTELLIGENT MEASUREMENT AND DIGITAL TRAINING SYSTEM

This application is a 371 of International Application No. PCT/CN2022/143225, entitled "HUMAN MOVEMENT INTELLIGENT MEASUREMENT AND DIGITAL TRAINING SYSTEM", filed Dec. 29, 2022, which claims priority to Chinese patent application No. 202210555949.2, entitled "HUMAN MOVEMENT INTELLIGENT MEASUREMENT AND DIGITAL TRAINING SYSTEM", filed May 20, 2022 with the China National Intellectual Property Administration, which are incorporated herein by reference in their entireties.

FIELD

The present disclosure relates to a system for intelligent measurement and digital training system of human motion, which belongs to the field of intelligent measurement in electronic industry. In the system, motion parameters are provided and training methods are improved.

BACKGROUND

As sports, science and technology continue to advance domestically, the innovation of a training mode for an athlete has become a crucial instrument for elevating a competitive level of the athlete. By advancing the training mode through science and technology, it has emerged as a key instrument for overcoming challenges in training.

It is necessary to monitor motion parameters of the athlete for improving motion methods and motion performance. In conventional technology, the method for monitoring the motion parameters uses technical means such as images. In such method, a motion process may only be roughly observed and determined, relying more on the experience from a professional coach, which fails to perform accurate quantitative analysis. Since most of motions at present have larger range, faster speed and higher requirements for the coordination of a whole body, a change in an angle between joints of the athlete has a strong correlation with a final motion effect. In order to measure the motion parameters of the athlete and provide quantitative technical support for technical improvement and performance improvement, it is necessary to utilize a wearable product to precisely measure the motion parameters and achieve intelligent data processing and analysis, which is convenient for the athlete and the coach to use. To make it convenient for the athlete and the coach to use, the athlete is only required to wear an inertial navigation system, while the coach is only required to operate a mobile phone or a PC to monitor the motion parameters of the athlete, with a support of a data comprehensive analysis system in the background, which is significantly simple to use and offers a key technical support for sports through science and technology.

SUMMARY

The technical problem solved by the present disclosure is to overcome the shortcomings in conventional technology. A system for intelligent measurement and digital training of human motion is provided, which measure parameters in a motion process and complete quantitative analysis in a training process.

The technical solutions of the present disclosure are described as follows. A system for intelligent measurement and digital training of human motion includes N inertial navigation wearable devices, M cameras, a data comprehensive analysis device and a terminal, where both N and M are greater than or equal to 1.

A total field of view of the M cameras is configured to cover a whole motion scene of an athlete, and the each camera is configured to capture an image in the field of view to form an image data frame and send the image data frame to the data comprehensive analysis device.

Each inertial navigation wearable device is secured on a limb of the athlete in a wearable manner, and each inertial navigation wearable device is configured to measure a three-axis linear acceleration of the limb of the athlete and a three-axis angular velocity of the limb of the athlete in an inertial coordinate system by taking the limb of the athlete as a carrier, and send the three-axis linear acceleration and the three-axis angular velocity to a data comprehensive analysis device.

The data comprehensive analysis device is configured to store basic information of the athlete, and establish and maintain an association relationship between the athlete and an inertial navigation wearable device the athlete wears; perform, based on the three-axis linear acceleration of the limb of the athlete and the three-axis angular velocity of the limb of the athlete in the inertial coordinate system, navigation solution and coordinate conversion to obtain and store a relative position and an attitude of the limb of the athlete in a body coordinate system of the athlete; collect and store the image captured by a respective camera, and perform target identification, tracking and coordinate conversion on the image captured by the respective camera to obtain and store a position and a speed of the athlete in a world coordinate system of the motion scene; and analyze the position and the speed of the athlete in the world coordinate system of the motion scene as well as the relative position and the attitude of the limb of the athlete in the body coordinate system of the athlete to determine and store motion parameters of the athlete.

The data comprehensive analysis device includes an inertial navigation solution device, a motion target detection and tracking device, a motion target speed identification device and a motion parameter analysis device.

The inertial navigation solution device is configured to perform, based on the three-axis linear acceleration of the limb of the athlete and the three-axis angular velocity of the limb of the athlete in the inertial coordinate system, the navigation solution to obtain attitude, speed and position information of the limb of the athlete in a navigation coordinate system; perform zero-velocity detection on motion of the limb of the athlete; and perform, in a case that the limb of the athlete is within a zero-velocity interval, zero-velocity error correction on the attitude, speed and position information of the limb of the athlete in the navigation coordinate system; and define the body coordinate system of the athlete, to convert the attitude, speed and position information of the limb of the athlete in the navigation coordinate system into corresponding information in the body coordinate system of the athlete.

The motion target detection and tracking device is configured to collect the image captured by the respective camera, record time for collecting the image, perform distortion correction on the image captured by the respective camera; perform target detection on each corrected image captured at a same time by using a you only look once (YOLO) model to obtain rough bounding boxes of all athletes in the image in a pixel coordinate system; obtain precise positions and precise bounding boxes of all athletes in the pixel coordinate system based on an edge detection method; and match precise bounding boxes of a respective athlete at different instants to track the precise bounding boxes of the respective athlete at different instants; convert coordinates of the respective athlete in the pixel coordinate system into coordinates in the world coordinate system corresponding to a coverage area of the field of view of the camera through a perspective projection matrix; calculate coordinates of the respective athlete in a global world coordinate system of the motion scene at different instants based on a position relationship among the coverage area of the field of view of the camera; and send the calculated coordinates to the motion target speed identification device.

The motion target speed identification device is configured to filter and denoise a coordinate sequence of the respective athlete in the global world coordinate system of the motion scene at different instants, and perform differential processing on the filtered and denoised coordinate sequence to obtain the speed of the athlete in the world coordinate system of the motion scene.

The motion parameter analysis device is configured to analyze the relative position and the attitude of the limb of the athlete in the body coordinate system of the athlete to obtain the motion parameters; compare positions and speeds of athletes in the world coordinate system of the motion scene, analyze and sort these data, and rank the athletes based on a determined rule; and perform contrast and comparison based on the motion parameters of the athlete and standard parameters.

The system for intelligent measurement and digital training of human motion further includes the terminal. The terminal is the terminal is configured to establish a three-dimensional model of the motion scene and a three-dimensional model of the athlete, associate a speed and a position of the athlete in a motion scene coordinate system as well as the relative position and the attitude of the limb of the athlete in the body coordinate system of the athlete with corresponding three-dimensional models, and display a motion process and the motion parameters of the athlete in a visualized manner.

The terminal is configured to support four types of identity users, including an athlete, a coach, an expert and an administrator; a terminal with an athlete permission includes an autonomous training device, a viewing history data device and a first group communication device, where the autonomous training device is configured to acquire real-time motion parameters from the data comprehensive analysis device and record the real-time motion parameters; the viewing history data device is configured to retrieve, based on a motion period and the basic information of the athlete, original images, motion parameters and a corresponding training evaluation of the motion period from the data comprehensive analysis device; and the first group communication device is configured to receive a message from the athlete for mutual communication with the coach and the expert.

The terminal with an coach permission includes an athlete management device, a competition management device and a second group communication device, wherein the athlete management device is configured to add or remove an athlete, and update the basic information of the athlete in the data comprehensive analysis device; the viewing history data device is further configured to retrieve, based on an externally inputted motion period and the basic information of the athlete, original images and motion parameters of the motion period from the data comprehensive analysis device, provide a training evaluation, and send the training evaluation to the data comprehensive analysis device for storage; the competition management device is configured to create a new intra-team contest, and send an intra-team contest grouping and a contest rule to the data comprehensive analysis device for storage; and the second group communication device is configured to receive a message from the coach for mutual communication with the athlete and the expert.

The terminal with an expert permission includes a training management device and a third group communication device, where the training management device is configured to view a ranking of training, compare motion parameters of athletes in a same game, evaluate and advise on the athletes and the training in the game, generate a data analysis report and send the data analysis report to the data comprehensive analysis device for storage; and the third group communication device is configured to receive a message from the expert for mutual communication with the coach and the athlete.

The terminal with an administrator identity is configured to set user information and a user identity.

Compared with the conventional art, the present disclosure is of the beneficial effects as follows.

1. According to the present disclosure, a wearable inertial navigation device is used to measure parameters during human motion process. The inertial navigation system is small in size, light in weight, low in power consumption and convenient to wear, which is not subjected to motion scenes of an athlete and measures motion parameters at any time.
2. According to the present disclosure, inertial navigation devices are arranged to different parts of a human body through straps, angular velocity information of a gyroscope and measurement information of an accelerometer are collected, and attitude information in a motion process is obtained through an inertial navigation algorithm and an error correction algorithm.
3. In an inertial navigation system according to the present disclosure, ESP8266 is used as a central processor, which is integrated with a wireless communication device, to achieve remote control and data acquisition.
4. According to the present disclosure, a pan-tilt-zoom camera is hung by an unmanned aerial vehicle to cover a whole motion scene of an athlete, and the athlete is dynamically tracked by using deep learning such as YOLO and DeepSORT, to calculate a relative position and a speed.
5. According to the present disclosure, a three-dimensional model is used to achieve the interaction between an athlete and the model, which can track the motion process of the athlete in real time and visualize and display the motion in a post-event inversion form.
6. According to the present disclosure, on the basis of precisely detecting a zero-velocity interval of each part, the inertial navigation wearable device is configured to periodically estimate and correct navigation errors of different measured parts of the human body through a zero-velocity error correction algorithm and an attitude error correction algorithm based on a Kalman filter, which solves a problem of error divergence of an MEMS sensor in a case of long-term use and improves measurement precision of the system.
7. According to the present disclosure, based on a fact that different parts, except for feet, such as thighs or calves also have different zero-velocity intervals in a walking process of a human body, an inertial navigation wearable device is configured to perform zero-velocity detection and correction algorithm on different limbs of an athlete, and further perform navigation error estimation and correction, which can solve the problem that navigation errors of other parts of the human body except for feet cannot be corrected regularly.

8. According to the present disclosure, based on motion data characteristics of different parts of a human body, an inertial navigation wearable device is configured to use different zero-velocity detection algorithms and set different energy thresholds, to precisely detect zero-velocity intervals of all the measured parts, including feet, thighs and calves, which can enable corrections of navigation errors of all parts on a regular basis.
9. According to the present disclosure, in a data comprehensive analysis device, further identifying a rough bounding box based on edge detection is added between YOLO model target identification and DeepSORT tracking to obtain a precise position and a precise bounding box of a target. Then, the precise bounding box is tracked by using DeepSORT, to improve the target detection and positioning precision. Hence, the device is suitable for a high-precision positioning case.
10. According to the present disclosure, in a data comprehensive analysis device, an "extended nine-point calibration method" is provided instead of a large calibration board, to achieve calibration with high precision in a wide range.
11. According to the present disclosure, in a data comprehensive analysis device, in a case of solving a perspective projection matrix, in order to accurately obtain a pixel coordinate of a mark point, the shape of mark point is set to be in shape of a rhombus. In this way, a relatively accurate angular position of the rhombus may be obtained in a captured image regardless of the capturing distance, to accurately position the center of the rhombus.

DETAILED DESCRIPTION OF EMBODIMENTS

Hereinafter, the description of the present disclosure is further provided in detail with reference to the drawings and specific embodiments.

Figure 1:
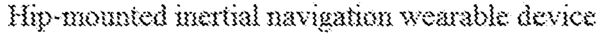
FIG. 1 is a schematic layout diagram of a system for intelligent measurement and digital training of human motion according to an embodiment of the present disclosure.
Figure 1:
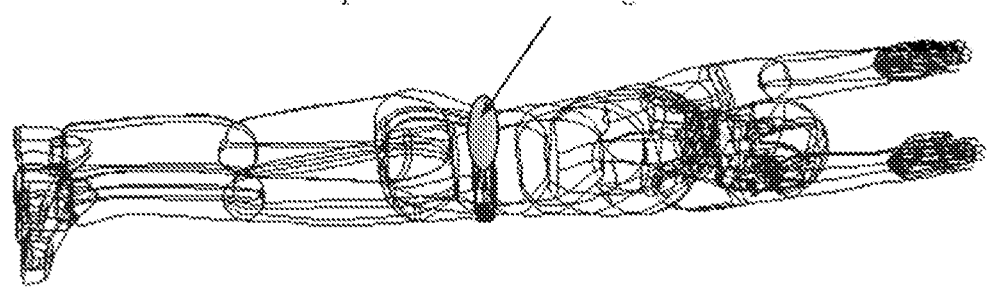

As shown in FIG. 1, according to the present disclosure, a system for intelligent measurement and digital training of human motion includes N inertial navigation wearable devices, M cameras, a data comprehensive analysis device and a terminal, where both N and M are greater than or equal to 1. The M cameras have a total field of view covering the whole motion scene of a motion target.

Each of the N inertial navigation wearable devices is secured on a limb of an athlete in a wearable manner, and is configured to measure a three-axis linear acceleration of the limb of the athlete and a three-axis angular velocity of the limb of the athlete in an inertial coordinate system by using the limb of the athlete as a carrier, and send the three-axis linear acceleration and the three-axis angular velocity to a data comprehensive analysis device; and receive an operating mode instruction sent by the data comprehensive analysis device to enable the inertial navigation wearable device to operate in different modes, including a data acquisition mode, a data storage mode, a real-time upload mode and an offline upload mode, etc.

The data comprehensive analysis device is configured to store basic information of an athlete, and establish and maintain an association relationship between the athlete and an inertial navigation wearable device worn by the athlete; perform, based on the three-axis linear acceleration of the limb of the athlete and the three-axis angular velocity of the limb of the athlete in the inertial coordinate system, navigation solution and coordinate conversion, to obtain a relative position and an attitude of the limb of the athlete in a body coordinate system of the athlete; collect images captured by the cameras, and perform target identification, tracking and coordinate conversion on the images captured by the cameras to obtain a position and a speed of the athlete in a world coordinate system of the motion scene; analyze the position and the speed of the athlete in the world coordinate system of the motion scene as well as the relative position and the attitude of the limb of the athlete in the body coordinate system of the athlete to determine motion parameters of the athlete; and receive a training instruction sent by the terminal, analyze the training instruction to obtain a training mode, and send instructions of different training modes to the athlete to guide the athlete to carry out reasonable training.

The terminal is configured to establish a three-dimensional model of the motion scene and a three-dimensional model of the athlete, associate a speed and a position of the athlete in a motion scene coordinate system as well as the relative position and the attitude of the limb of the athlete in the body coordinate system of the athlete with the corresponding three-dimensional models, and display a motion process and the motion parameters of the athlete in a visualized manner; and send a training instruction inputted by a coach to the data comprehensive analysis device.

Figure 2:
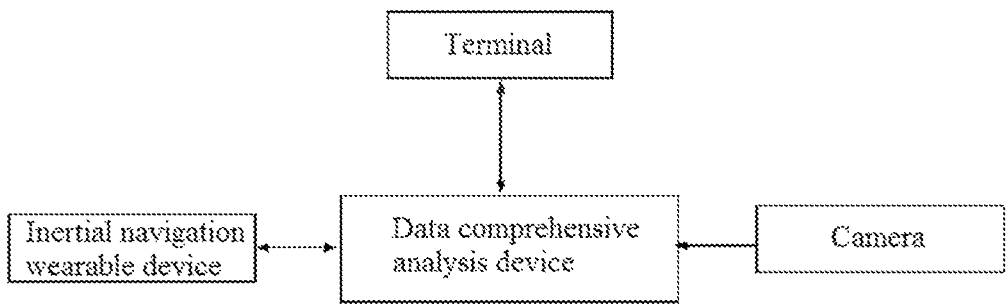
FIG. 2 is a schematic diagram of an inertial navigation system arranged on a hip of an athlete according to an embodiment of the present disclosure.

As shown in FIG. 2, an inertial navigation wearable device may be bound to a hip, an arm, a thigh, a calf, a foot and other parts of an athlete through strapping or sticking. An origin of a body coordinate system of the athlete coincides with a center of gravity of a human body, a X-axis is perpendicular to a sagittal plane, the Y-axis is perpendicular to a coronal plane, and a Z-axis is perpendicular to a transverse plane.

The coronal plane divides the human body into front and back complete sections. The sagittal plane is parallel to a direction of the view of human, which divides the human body into left and right symmetrical parts. The transverse plane, also known as a horizontal plane, indicates that the horizontal surface of Earth divides the human body into upper and lower parts.

A wireless mode is used for data transmission between the data comprehensive analysis device, the inertial navigation wearable devices and the terminal.

A wired mode is used for data transmission between the data comprehensive analysis device and the cameras.

Before the athlete starts to exercise, the coach controls an inertial navigation system worn on the athlete to be in an operating mode through the terminal. At this time, the athlete may exercise as required, and the coach may view parameters of the motion process in real time through a mobile phone or a PC data terminal.

In a case that a training is finished, the coach controls the inertial navigation system to be in a sleep state or stop operating through the terminal.

The technical points of the present disclosure are described in detail below.

1. Inertial Navigation Wearable Device

The inertial navigation wearable device is worn on the athlete and configured to measure attitude information of the athlete in the whole training process. The inertial navigation wearable device includes an MEMS sensor, a signal processing device, a communication device and a lithium battery.

The MEMS sensor is internally integrated with an MEMS gyroscope and an MEMS accelerometer, where the MEMS gyroscope is configured to output the three-axis angular velocity in the inertial coordinate system, and the MEMS accelerometer is configured to output the three-axis linear acceleration of the limb of the athlete, and the MEMS sensor is configured to output measurement results to the signal processing device.

The signal processing device is configured to frame and package the measurement results outputted by the MEMS sensor and send them to the communication device.

The communication device is configured to send a packaged measurement data frame by wireless communication.

The lithium battery is configured to supply power for the MEMS sensor, the signal processing device and the communication device.

In a specific embodiment of the present disclosure, the inertial navigation wearable device includes an MTI-3 attitude sensor, a processing circuit centered on ESP8266, a lithium battery and the like, and is configured to measure an attitude of an athlete. The MTI-3 attitude sensor utilizes a highly integrated MTI-3 micro inertial sensing unit, which integrates information of a three-axis gyroscope, a three-axis accelerometer and the like, with the characteristics of small in size and light in weight.

The inertial navigation wearable devices are worn on different limb parts of one or more athletes, and data outputted by the N inertial navigation wearable devices are synchronous, so that motion intelligent measurement and digital training may be performed on N athletes simultaneously.

If the athlete swims, the inertial navigation wearable device may also be of a waterproof function, where upper and lower housing structures of the inertial navigation wearable device may be sealed by silicone rubber to achieve IP68 waterproof rating.

2. Camera

In a specific embodiment of the present disclosure, one or more cameras are arranged over the motion scene to accommodate physical features of the athlete. The one or more cameras configured to capture a video of training the athlete in a complex environment of training the athlete. A series of image analysis, processing and tracking are performed on the video, to finally achieve functions of target identification, positioning and speed measurement for the athlete.

3. Data Comprehensive Analysis Device

The data comprehensive analysis device may include an inertial navigation solution device, a motion target detection and tracking device, a motion target speed identification device and a motion parameter analysis device.

The inertial navigation solution device is configured to perform, based on the three-axis linear acceleration and the three-axis angular velocity of the limb of the athlete in the inertial coordinate system, the navigation solution to obtain attitude, speed and position information of the limb of the athlete in a navigation coordinate system; perform zero-velocity detection on motion of the limb of the athlete, and perform, in a case that the limb of the athlete is within a zero-velocity interval, zero-velocity error correction on the attitude, speed and position information of the limb of the athlete in the navigation coordinate system; and define the body coordinate system of the athlete, to convert the attitude, speed and position information of the limb of the athlete in the navigation coordinate system to those in the body coordinate system of the athlete.

The motion target detection and tracking device is configured to collect images captured by the cameras, record time for collecting the respective images; perform distortion correction on the images captured by the cameras; perform target detection on each of corrected images captured at a same moment by using a YOLO model to obtain rough bounding boxes of all athletes in the image in a pixel coordinate system; and obtain precise position and precise bounding box of each athlete in the pixel coordinate system based on an edge detection method; and then, match precise bounding boxes of a same athlete at different instants to track the precise bounding boxes of the athlete at different instants; convert coordinates of the athlete in the pixel coordinate system into coordinates in the world coordinate system corresponding to the coverage area of the field of view of the cameras through the perspective projection matrix; calculate coordinates of the respective athlete in a global world coordinate system of the motion scene at different moments based on a position relationship between coverage areas of the field of view of the cameras, and send the calculated coordinates to the motion target speed identification device.

The motion target speed identification device is configured to filter and denoise a coordinate sequence of the respective athlete in the global world coordinate system of the motion scene at different instants, and perform differential processing on the filtered and denoised coordinate sequence to obtain the speed of the respective athlete in the world coordinate system of the motion scene.

The motion parameter analysis device is configured to analyze the relative position and the attitude of the limb of the athlete in the body coordinate system of the athlete to obtain the motion parameters; compare positions and speeds of athletes in the world coordinate system of the motion scene, analyze and sort these data, and rank the athletes based on a determined rule; and analyze a comparison between the motion parameters of the athlete and standard motion parameters simultaneously, which is convenient for the coach to analyze the shortcomings of the athlete and improve the training process.

3.1 Inertial Navigation Solution Device

In the present disclosure, an "east-north-up (ENU)" geographical coordinate system is selected as the navigation coordinate system, and the navigation solution is performed by using a recursive updating algorithm, to obtain the attitude, speed and position information of the limb of the athlete in the navigation coordinate system. An inertial navigation updating algorithm is divided into three parts: attitude, speed and position updating, and the attitude updating algorithm is the core part.

Figure 3:
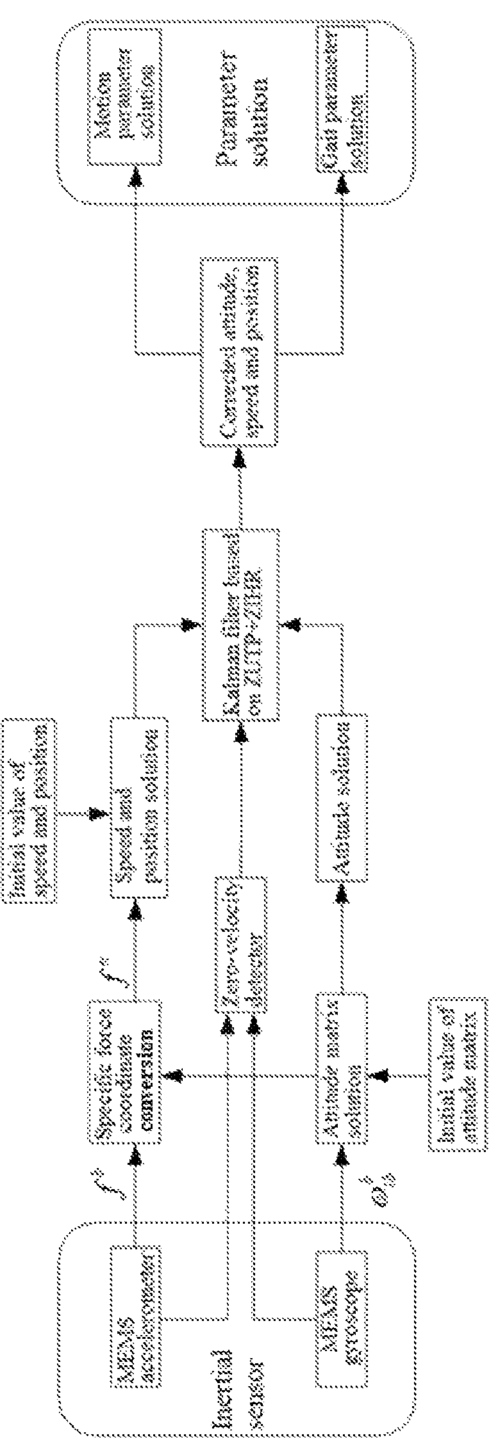
FIG. 3 is a schematic diagram of a system for measuring a human motion attitude according to an embodiment of the present disclosure.

As shown in FIG. 3, the inertial navigation solution device is implemented by steps S1 to S6 as follows.

In S1, an "east-north-up" geographical coordinate system is selected as the navigation coordinate system, the three-axis linear acceleration of the limb of the athlete and the three-axis angular velocity of the limb of the athlete in the inertial coordinate system are acquired; and the navigation solution is performed to obtain the attitude, speed and position information of the limb of the athlete in the navigation coordinate system.

In S1.1, the three-axis angular velocity $$\omega_{ib}^{b}$$

of the limb of the athlete in the inertial coordinate system is acquired.

In S1.2, based on the three-axis angular velocity $$\omega_{ib}^{b}$$

of the limb of the athlete in the inertial coordinate system, a three-axis angular velocity $$\omega_{nb}^{b}$$

of the limb of the athlete in the navigation coordinate system is calculated.

An angular velocity equation is expressed by:

$$\omega_{nb}^{b}=\omega_{ib}^{b}-\omega_{ie}^{b}-\omega_{en}^{b}$$

where, $$\omega_{nb}^{b}$$

is a projection of an angular velocity of a carrier coordinate system relative to the navigation coordinate system in the carrier coordinate system, $$\omega_{ib}^{b}$$

is a projection of an angular velocity of the carrier coordinate system relative to the inertial coordinate system in the carrier coordinate system, $$\omega_{ie}^{b}$$

is a projection of an angular velocity of an Earth coordinate system relative to the inertial coordinate system in the carrier coordinate system, and $$\omega_{en}^{b}$$

is a projection of an angular velocity of the navigation coordinate system relative to the Earth coordinate system in the carrier coordinate system.

Since the MEMS sensor has low precision and may not be sensitive to an angular velocity of an rotation of Earth, $$w_{ie}^{b}$$

may be ignored. In general, since the speed of a person in a motion scene or a walking scene is less than 10 m/s, a radius of Earth R=6371393m, and $$w_{en}^{b}=\frac{V_{en}^{b}}{R},\ w_{en}^{b}$$

is of a magnitude of $10^{-7}$ to $10^{-6}$, which may also be ignored. Hence, for the MEMS sensor, the above equation may be equivalent to:

$$\omega_{nb}^{b}=\omega_{ib}^{b}.$$

In S1.3, an attitude quaternion $Q_k$ of the limb of the athlete at a current sampling instant is calculated, and $Q_k=[q_1\ q_2\ q_3\ q_4]$:

$$Q_k=\frac{1}{2}\begin{bmatrix} 2 & -\omega_{nbx}^{b}\times\Delta t & -\omega_{nby}^{b}\times\Delta t & -\omega_{nbz}^{b}\times\Delta t \\ \omega_{nbx}^{b}\times\Delta t & 2 & \omega_{nbz}^{b}\times\Delta t & -\omega_{nby}^{b}\times\Delta t \\ \omega_{nby}^{b}\times\Delta t & -\omega_{nbz}^{b}\times\Delta t & 2 & \omega_{nbx}^{b}\times\Delta t \\ \omega_{nbz}^{b}\times\Delta t & \omega_{nby}^{b}\times\Delta t & -\omega_{nbx}^{b}\times\Delta t & 2 \end{bmatrix}Q_{k-1};$$

where, Δt is a sampling interval of the three-axis angular velocity $$\omega_{ib}^{b}$$

in the inertial coordinate system, i.e., an output interval of the MEMS sensor, and $Q_{k-1}$ is an attitude quaternion of the limb of the athlete at a previous sampling instant.

An initial value of $Q_k$ is calculated by initial attitude angles $\theta_0$, $\gamma_0$, $\psi_0$ of the limb of the athlete in the navigation coordinate system obtained by initial alignment, and then by a quaternion which is constantly updated.

In S1.4, a coordinate conversion matrix $$C_b^n$$

from the body coordinate system of the limb of the athlete to the navigation coordinate system is calculated, based on the attitude quaternion $Q_k$ of the limb of the athlete at the current sampling instant.

In S1.5, the attitude of the limb of the athlete in the navigation coordinate system is calculated based on the coordinate conversion matrix $$C_b^n$$

from the body coordinate system of the limb of the athlete to the navigation coordinate system, where the attitude of the limb of the athlete in the navigation coordinate system includes a pitch angle θ, a roll angle γ and a yaw angle ψ of the limb of the athlete.

In one embodiment, based on $$(C_b^n)^T = \begin{bmatrix} T_{11} & T_{12} & T_{13} \\ T_{21} & T_{22} & T_{23} \\ T_{31} & T_{32} & T_{33} \end{bmatrix},$$

the pitch angle θ, the roll angle γ and the yaw angle ψ of the limb of the athlete are derived as follows:

$$\begin{aligned} \theta &= \arcsin(T_{32}) \\ \gamma &= \arctan\left(-\frac{T_{31}}{T_{33}}\right). \\ \psi &= rc\tan\left(\frac{T_{12}}{T_{22}}\right) \end{aligned}$$

In S1.6, the coordinate conversion matrix $$C_b^n$$

from the body coordinate system of the limb of the athlete to the navigation coordinate system is substituted into a specific force equation to obtain $$\dot{V}_{en}^n,$$

i.e., a projection of an acceleration of the navigation coordinate system relative to Earth coordinate system in the navigation coordinate system.

The specific force equation is expressed by:

$$\dot{V}_{en}^n = C_b^n \times f^b - (2\omega_{ie}^n + \omega_{en}^n) \times V_{en}^n + g^n$$

where, $f^b$ is the three-axis linear acceleration of the limb of the athlete in the inertial coordinate system, $$\omega_{ie}^n$$

is a projection of an angular velocity of the Earth coordinate system relative to the inertial coordinate system in the navigation coordinate system, $$\omega_{en}^n$$

is a projection of an angular velocity of the navigation coordinate system relative to the Earth coordinate system in the navigation coordinate system, and $g^n$ is a projection of a gravity acceleration in the navigation coordinate system.

Since a motion speed of a person in a general scene is less than 10 m/s, the projection $$\omega_{ie}^n$$

of the angular velocity of the Earth coordinate system relative to the inertial coordinate system in the navigation coordinate system, the projection $$V_{en}^n$$

of a speed of the navigation coordinate system relative to the Earth coordinate system in the navigation coordinate system and the projection $$\omega_{en}^n$$

of the angular velocity of the navigation coordinate system relative to the Earth coordinate system in the navigation coordinate system may be ignored, and $g^n$ is the projection of the gravity acceleration in the navigation coordinate system, as a result, $$\dot{V}_{en}^n$$

may be calculated, i.e., a projection of an acceleration of a human body relative to the Earth in the navigation coordinate system may be calculated.

In S1.7, based on equation $$V_{en,k}^n = V_{en,k-1}^n + \dot{V}_{en}^n \cdot \Delta t,$$

a projection of the speed of the navigation coordinate system relative to the Earth coordinate system in the navigation coordinate system, i.e., the speed of the limb of the athlete in the navigation coordinate system is updated, where $$V_{en,k-1}^n$$

is a projection of a speed of the navigation coordinate system relative to the Earth coordinate system in the navigation coordinate system at a previous sampling instant, and $$V^n_{en,k}$$

is a projection of a speed of the navigation coordinate system relative to the Earth coordinate system in the navigation coordinate system at a current sampling instant.

In S1.7, the position of the limb of the athlete in the navigation coordinate system is updated based on:

$$P_k = P_{k-1} + V^n_{en,k-1} \cdot \Delta t$$

where Δt is a sampling interval of an MEMS sensor, $P_{k-1}$ is a position at a previous sampling instant, $P_k$ is a position at a current sampling instant, and $$V^n_{en,k-1}$$

is a projection of a speed of the navigation coordinate system relative to the Earth coordinate system in the navigation coordinate system at the previous sampling instant.

In S2, a Kalman filter is established by determining an attitude angle error, a speed error and a position error of the limb of the athlete in the navigation coordinate system, gyro zero bias and accelerometer zero bias in the MEMS sensor as state variables and determining a speed error and an attitude error of the limb of the athlete in the zero-velocity interval as measurements.

The state variables X in a Kalman filtering method are:

$$X = [\varphi_x \ \ \varphi_y \ \ \varphi_z \ \ \delta v_x \ \ \delta v_y \ \ \delta v_z \ \ \delta x \ \ \delta y \ \ \delta z \ \ \varepsilon_{bx} \ \ \varepsilon_{by} \ \ \varepsilon_{bz} \ \ \nabla_{bx} \ \ \nabla_{by} \ \ \nabla_{bz}]$$

where, $\varphi_x$ $\varphi_y$ $\varphi_z$ are the attitude angle errors of the limb of the athlete in the navigation coordinate system, $\delta v_x$ $\delta v_y$ $\delta v_z$ are the speed errors of the limb of the athlete in the navigation coordinate system, δx δy δz are the position errors of the limb of the athlete in the navigation coordinate system, $\varepsilon_{bx}$ $\varepsilon_{by}$ $\varepsilon_{bz}$ are the gyro zero biases, and $\nabla_{bx}$ $\nabla_{by}$ $\nabla_{bz}$ are the accelerometer zero biases.

A state equation is expressed by:

$$X_k = \Phi_{k/k-1} X_{k-1} + \Gamma_{k-1} W_{k-1}$$

where, X is a state variable, Φ is a one-step transition matrix, Γ is a process noise distribution matrix, W is a process noise matrix, k−1 and k respectively are a (k−1)-th sampling instant and a k-th sampling instant, and k/k−1 is a one-step prediction from the (k−1)-th sampling instant to the k-th sampling instant.

$$\Phi = \begin{bmatrix} F_{11} & F_{12} \\ O_{6\times 9} & O_{6\times 6} \end{bmatrix}_{15\times 15}$$

-continued $$F_{11} = \begin{bmatrix} O_{3\times 3} & O_{3\times 3} & O_{3\times 3} \\ f^n \times & O_{3\times 3} & O_{3\times 3} \\ O_{3\times 3} & I_{3\times 3} & O_{3\times 3} \end{bmatrix}$$

$$F_{12} = \begin{bmatrix} -C^n_b & O_{3\times 3} \\ O_{3\times 3} & C^n_b \\ O_{3\times 3} & O_{3\times 3} \end{bmatrix}$$

$$W = [w_{gx} \ \ w_{gy} \ \ w_{gz} \ \ w_{ax} \ \ w_{ay} \ \ w_{az}]^T$$

where, W is a process noise matrix, $w_{gx}$, $w_{gy}$ and $w_{gz}$ respectively are noises of a three-axis gyroscope, $w_{ax}$, $w_{ay}$ and $w_{az}$ are noises of a three-axis accelerometer, $$(f^n \times) = \begin{bmatrix} 0 & -f^n_z & f^n_y \\ f^n_z & 0 & -f^n_x \\ -f^n_y & f^n_y & 0 \end{bmatrix}$$

is an antisymmetric matrix composed of $$f^n = [f^n_x, f^n_y, f^n_z];$$

and $$f^n_x, f^n_y, f^n_z$$

are the three-axis linear acceleration of the carrier in the navigation coordinate system. The process noise distribution matrix Γ is expressed by:

$$\Gamma = \begin{bmatrix} -C^n_b & O_{3\times 3} \\ O_{3\times 3} & C^n_b \\ O_{9\times 3} & O_{9\times 3} \end{bmatrix}_{15\times 6}.$$

The measurements are:

$$Z_k = \begin{bmatrix} V_x - 0 \\ V_y - 0 \\ V_z - 0 \\ \psi_{Z_k} - \psi_{Z_{k-1}} \end{bmatrix}$$

where $V_x$, $V_y$ and $V_z$ respectively are three-axis components of the speed of the limb of the athlete in the navigation coordinate system;

$\psi_{Z_k}$ and $\psi_{Z_{k-1}}$, respectively are attitude angle data of the limb of the athlete at a previous sampling instant and a current sampling instant.

Measurement equations are:

$$Z_k = H_k X_k + U_k;$$

$$H = \begin{bmatrix} O_{3\times 3} & I_{3\times 3} & O_{3\times 3} & O_{3\times 3} & O_{3\times 3} \\ H_{21} & O_{1\times 3} & O_{1\times 3} & H_{24} & O_{1\times 3} \end{bmatrix};$$

$$H_{21} = [0 \ \ 0 \ \ -\omega_{ie}\tan\gamma\cos\psi\cos L\Delta t]$$

$$H_{24} = [0 \ \ \sec\gamma\sin\theta\Delta t \ \ \sec\gamma\cos\theta\Delta t]$$

-continued $$U = \left[ w_{\delta v_x} \quad w_{\delta v_y} \quad w_{\delta v_z} \quad w_{\delta \psi_z} \right]^T,$$

where, $\omega_{ie}$ is an angular velocity of the Earth rotation, L is a latitude of the Earth where the carrier is located, U is a measurement noise matrix; $w_{\delta v_x}$, $w_{\delta v_y}$ and $w_{\delta v_z}$ respectively are three-axis velocity error noises, $w_{\delta \psi_z}$ is an attitude angle error noise, θ, γ and ψ respectively are a pitch angle, a roll angle and a yaw angle of the limb of the athlete, and Δt is a sampling interval of the MEMS sensor.

In S3, at each sampling instant of the MEMS sensor, one-step prediction of the state variables of the Kalman filter is performed, a state one-step prediction error covariance matrix is calculated, proceeding to step S4.

In S4, whether the limb of the athlete is within the zero-velocity interval is determined, in a case that the limb of the athlete is within the zero-velocity interval, step S5 is executed; otherwise, step S6 is executed.

Low precision of an MEMS inertial sensor is a main error factor that undermines navigation precision of the system. In a case that the MEMS inertial sensor is used for a long time, a navigation error accumulates over time, which seriously undermines accuracy of a final measurement result. Different zero-velocity detection algorithms are used to detect a static interval of a human body in motion, and then a parameter is corrected in a zero-velocity interval, which may effectively eliminate a speed error and constrain position and heading errors In a process of walking, with feet lifting, stepping, landing and standing still, IMU sensors worn on different parts of the human body may also be sensitive to periodic changes in corresponding parts. Through an analysis, besides the feet, thighs, calves and other parts of the human body also have periodic zero-velocity intervals in the process of walking. Different detection algorithms and targeted energy thresholds may be used to detect the periodic zero-velocity intervals of different parts of the human body.

According to the present disclosure, determining whether a speed of the limb of the athlete is within the zero-velocity interval includes:

sending raw data outputted by an MEMS gyroscope and an MEMS accelerometer to a zero-velocity detector; and calculating, by the zero-velocity detector, statistical magnitude of motion energy of the limb of the athlete; setting a threshold of the zero-velocity detector; determining that the limb of the athlete is within the zero-velocity interval, in a case that the statistical magnitude of the zero-velocity detector is lower than the preset threshold of the zero-velocity detector; and determining that the limb of the athlete is outside the zero-velocity interval, in a case that the statistical magnitude of the zero-velocity detector is not lower than the preset threshold of the zero-velocity detector.

For different limbs of the athlete, the zero-velocity detector calculates energy statistical values of motion of the limbs of the athlete with different algorithms. In an embodiment, in a case that the limbs of the athlete are human feet, the zero-velocity detector calculates the energy statistical values with a GLRT or ARE algorithm. In a case that the limbs of the athlete are human thighs or calves, the zero-velocity detector calculates the energy statistical values with an MAG or MV algorithm.

In a specific embodiment of the present disclosure, based on motion data features of different parts of the human body during the motion, GLRT algorithm may be used as a zero-velocity detection algorithm for the foot, and an energy detection threshold may be set to 25000; MAG algorithm may be used as a zero-velocity detection algorithm for the calf and an energy detection threshold may be set to 1000; and MAG algorithm may be used as a zero-velocity detection algorithm for the thigh, and an energy detection threshold may be set to 750. Through different zero-velocity detection algorithms and appropriate setting of energy detection thresholds, zero-velocity intervals of corresponding parts may be effectively detected, i.e., energy statistical values of motion of the limbs of the athlete are less than detection thresholds.

In S5, the measurements and a measurement matrix of the Kalman filter are updated; a filtering gain is calculated and a state estimate error covariance matrix is updated based on the measurements, the state one-step prediction error covariance matrix, the state estimate error covariance matrix and the measurement noise covariance matrix, the state estimate is performed by the filtering gain and the measurement matrix to obtain the speed error, the position error and the attitude angle error of the limb of the athlete in the navigation coordinate system; and then, the attitude, speed and position information of the limb of the athlete in the navigation coordinate system are corrected based on the estimated errors.

In S6, the attitude, speed and position information of the limb of the athlete in the navigation coordinate system is outputted.

The details of the Kalman filtering and zero-velocity error correction algorithm according to the present disclosure are described below.

The principle of Kalman filtering is to use a speed error and an attitude angle error in a zero-velocity interval as observation measurements to establish a Kalman filter, to estimate a speed error, a position error and an attitude angle error of a limb of an athlete, and compensate the estimated errors into corresponding variables to obtain each estimate approximate to the true value of respective state variable.

The state variable of the Kalman filter includes a speed error, a position error and an attitude error. Hence, it is required to establish an appropriate state equation based on an error equation of inertial navigation, a characteristic of an MEMS sensor and a feature of human motion.

3.1 Error Equation (a) Attitude Error Equation

An MEMS attitude error equation is expressed by:

$$\dot{\phi} = -C_b^n \varepsilon^b$$

where, ϕ is an attitude angle error, and $\varepsilon^b$ is a gyro zero bias.

(b) Speed Error Equation

An MEMS speed error equation is expressed by:

$$\delta V = f^n \times \phi + C_b^n \nabla^b$$

where, δV is a speed error, $f^n$ is a projection of an acceleration in the navigation coordinate system, and $\nabla^b$ is a accelerometer zero bias.

(c) Position Error Equation

An MEMS position error equation is expressed by:

$$\delta\dot{P} = \delta V$$

where, δP is a position error, and δV is a speed error.

3.2 Correction Algorithm and Measurement Equation (a) Zero-Velocity Error Correction In a case of detecting that motion is in a static stage, its real speed should be zero theoretically. However, due to a large measurement error of an MEMS sensor, a speed obtained by MEMS inertial navigation solution is actually not zero. A zero-velocity error correction method includes treating a speed obtained by MEMS inertial navigation solution in a static stage as a speed error, and performing Kalman filtering estimation on the speed error as a measurement, to suppress a navigation parameter error.

Therefore, the speed error based on the zero-velocity error correction algorithm is ΔV, and $$\Delta V = \begin{bmatrix} V_x - 0 \\ V_y - 0 \\ V_z - 0 \end{bmatrix}$$

where, $V_x$, $V_y$ and $V_z$ respectively are three-axis components of a speed value of the limb of the athlete obtained by navigation solution.

(b) Attitude Error Correction

In a static stage, theoretically, an attitude angle will not change at previous and subsequent instants. Similarly, due to a relatively large measurement error of an MEMS sensor, a difference of the attitude angle between the previous instant and subsequent instant is calculated to be not zero. Hence, the difference of the attitude angle between the previous instant and subsequent instant in a zero-velocity interval may be treated as a measurement, to suppress an attitude angle error.

Therefore, the measurement based on the attitude error correction algorithm is $\psi_{Z_k}-\psi_{Z_{k-1}}$, and $\psi_{Z_k}-\psi_{Z_{k-1}}=-\omega_{ie}\tan\gamma\cos_{\psi}\delta_{\varphi_Z}\cos L\Delta t+\sec\gamma\sin\theta\varepsilon_{by}\Delta t+\sec\gamma\cos\theta\varepsilon_{bz}\Delta t$;

where, $\omega_{ie}$ is an angular velocity of the rotation of Earth, and L is a latitude of Earth where the measured human body is located.

3.3 Kalman Filtering (a) State Equation

Based on the attitude error equation, the speed error equation and the position error equation, an expression of the state equation may be obtained:

$$X_k = \Phi_{k/k-1}X_{k-1} + \Gamma_{k-1}W_{k-1}$$

where, X is a state variable, Φ is a one-step transition matrix, Γ is a process noise distribution matrix, W is a process noise matrix, k−1 and k respectively are a (k−1)-th sampling instant and a k-th sampling instant, and k/k−1 is a one-step prediction from the (k−1)-th sampling instant to the k-th sampling instant.

$$X = [\varphi_x \ \varphi_y \ \varphi_z \ \delta v_x \ \delta v_y \ \delta v_z \ \delta x \ \delta y \ \delta z \ \varepsilon_{bx} \ \varepsilon_{by} \ \varepsilon_{bz} \ \nabla_{bx} \ \nabla_{by} \ \nabla_{bz}] \quad (19)$$

where, $\varphi_x$ $\varphi_y$ $\varphi_z$ are the attitude angle errors of the limb of the athlete in the navigation coordinate system, $\delta v_x$ $\delta v_y$ $\delta v_z$ are the speed errors of the limb of the athlete in the navigation coordinate system, δx δy δz are the position errors of the limb of the athlete in the navigation coordinate system, $\varepsilon_{bx}$ $\varepsilon_{by}$ $\varepsilon_{bz}$ are the gyro zero biases, and $\nabla_{bx}$ $\nabla_{by}$ $\nabla_{bz}$ are the accelerometer zero biases.

The one-step transition matrix is expressed by:

$$\Phi = \begin{bmatrix} F_{11} & F_{12} \\ O_{6\times9} & O_{6\times6} \end{bmatrix}_{15\times15}$$

$$F_{11} = \begin{bmatrix} O_{3\times3} & O_{3\times3} & O_{3\times3} \\ f^n\times & O_{3\times3} & O_{3\times3} \\ O_{3\times3} & I_{3\times3} & O_{3\times3} \end{bmatrix}$$

$$F_{12} = \begin{bmatrix} -C_b^n & O_{3\times3} \\ O_{3\times3} & C_b^n \\ O_{3\times3} & O_{3\times3} \end{bmatrix}.$$

The process noise matrix is expressed by:

$$W = [w_{gx} \ w_{gy} \ w_{gz} \ w_{ax} \ w_{ay} \ w_{az}]^T$$

where, W is a process noise, $w_{gx}$, $w_{gy}$ and $w_{gz}$ respectively are noises of the three-axis gyroscope, $w_{ax}$, $w_{ay}$ and $w_{az}$ are noises of the three-axis accelerometer, $$(f^n\times) = \begin{bmatrix} 0 & -f_z^n & f_y^n \\ f_z^n & 0 & -f_x^n \\ -f_y^n & f_y^n & 0 \end{bmatrix}$$

is an antisymmetric matrix composed of $$f^n = [f_x^n, f_y^n, f_z^n];$$

and $$f_x^n, f_y^n, f_z^n$$

are the three-axis acceleration of the carrier in the navigation coordinate system.

The process noise distribution matrix is expressed by:

$$\Gamma = \begin{bmatrix} -C_b^n & O_{3\times3} \\ O_{3\times3} & C_b^n \\ O_{9\times3} & O_{9\times3} \end{bmatrix}_{15\times6}.$$

(b) Measurement Equation

Based on the zero-velocity error correction and the attitude error correction, an expression of the measurement equation may be obtained by:

$$Z_k = H_k X_k + U_k$$

where, the measurements are:

$$Z_k = \begin{bmatrix} V_x - 0 \\ V_y - 0 \\ V_z - 0 \\ \psi_{Z_k} - \psi_{Z_{k-1}} \end{bmatrix}$$

where, $V_x$, $V_y$ and $V_z$ respectively are three-axis components of the speed of the limb of the athlete in the navigation coordinate system;

$\psi_{Z_k}$ and $\psi_{Z_{k-1}}$ respectively are attitude angle data of the limb of the athlete at a previous sampling instant and a current sampling instant.

The measurement matrix is expressed by:

$$H = \begin{bmatrix} O_{3\times3} & I_{3\times3} & O_{3\times3} & O_{3\times3} & O_{3\times3} \\ H_{21} & O_{1\times3} & O_{1\times3} & H_{24} & O_{1\times3} \end{bmatrix}$$

$$H_{21} = [0 \;\; 0 \;\; -\omega_{ie} \tan\gamma \cos\psi \cos L\Delta t]$$

$$H_{24} = [0 \;\; \sec\gamma \sin\theta\Delta t \;\; \sec\gamma \cos\theta\Delta t]$$

where, $\omega_{ie}$ is the angular velocity of the rotation of Earth, L is a latitude of Earth where the carrier is located, $\theta$, $\gamma$ and $\psi$ respectively are the pitch angle, the roll angle and the yaw angle of the limb of the athlete, and $\Delta t$ is the sampling interval of the MEMS sensor.

The measurement noise matrix U is expressed by:

$$U = \begin{bmatrix} w_{\delta v_x} & w_{\delta v_y} & w_{\delta v_z} & w_{\delta\psi_z} \end{bmatrix}^T$$

where, $w_{\delta v_x}$, $w_{\delta v_y}$ and $w_{\delta v_z}$ respectively are three-axis speed error noises, and $w_{67\ \psi_z}$ is an attitude angle error noise.

(c) Filtering Algorithm

Based on the Kalman filtering algorithm, a continuous equation is discretized and substituted into the following formula.

A state one-step prediction is expressed by:

$$\hat{X}_{k/k-1} = \Phi_{k/k-1}\hat{X}_{k-1}$$

where, $\hat{X}_{k-1}$ is an optimal state estimate at a previous sampling instant, is a $\hat{X}_{k/k-1}$ is a state estimate from the previous sampling instant to a current sampling instant, and $\Phi_{k/k-1}$ is a one-step transition matrix from the previous sampling instant to the current sampling instant.

A state one-step prediction error covariance matrix is expressed by:

$$P_{k/k-1} = \Phi_{k/k-1}P_{k-1}\Phi_{k/k-1}^T + \Gamma_{k-1}Q_{k-1}\Gamma_{k-1}^T$$

where, $P_{k/k-1}$ is an error covariance matrix from the previous sampling instant to the current instant, $P_{k-1}$ is an error covariance matrix at the previous sampling instant, $\Gamma_{k-1}$ is a process noise distribution matrix at the previous sampling instant, and $Q_{k-1}$ is a process noise covariance matrix at the previous sampling instant.

A filtering gain is expressed by:

$$K_k = P_{k/k-1}H_k^T\left(H_k P_{k/k-1} H_k^T + R_k\right)^{-1}$$

where, $K_k$ is a filtering gain at the current sampling instant, $P_{k/k-1}$ is an error covariance matrix from the previous sampling instant to the current instant, $H_k$ is a measurement matrix at the current sampling instant, and $R_k$ is a measurement noise covariance matrix at the current sampling instant.

A state estimate is expressed by:

$$\hat{X}_k = \hat{X}_{k/k-1} + K_k\left(Z_k - H_k\hat{X}_{k/k-1}\right)$$

where, $\hat{X}_k$ is an optimal state estimate at the current sampling instant, $\hat{X}_{k/k-1}$ is a state estimate from the previous sampling instant to the current sampling instant, $K_k$ is a filtering gain at the current sampling instant, $Z_k$ is measurement at the current sampling instant, and $H_k$ is a measurement matrix at the current sampling instant.

A state estimate error covariance matrix is expressed by:

$$P_k = (I - K_k H_k)P_{k/k-1}$$

where, $P_k$ is an error covariance matrix at the current sampling instant, $P_{k/k-1}$ is the error covariance matrix from the previous sampling instant to the current sampling instant, I is a unit matrix, $K_k$ is a filtering gain at the current sampling instant, and $H_k$ is the measurement matrix at the current sampling instant.

Since the zero-velocity measurements are only available in the zero-velocity interval, the Kalman filter only performs time update and does not perform measurement update outside the zero-velocity interval. After the zero-velocity interval is detected, the filter performs time and measurement updates.

3.2 Motion Target Detection and Tracking Device

The principle of camera imaging is expressed by the equation below:

$$Z_C\begin{bmatrix}u\\v\\1\end{bmatrix}=\begin{bmatrix}f_x & 0 & u_0 & 0\\0 & f_y & v_0 & 0\\0 & 0 & 1 & 0\end{bmatrix}\begin{bmatrix}R & T\\\vec{0} & 1\end{bmatrix}\begin{bmatrix}X_w\\Y_w\\Z_w\\1\end{bmatrix}=M_1M_2\begin{bmatrix}X_w\\Y_w\\Z_w\\1\end{bmatrix}$$

where, (u, v) is pixel coordinates, and ($X_w$, $Y_w$, $Z_w$) is world coordinates.

$M_1$ is an intrinsic matrix. $f_x$=f/dx refers to a normalized focal length in a x-axis direction of a camera, and $f_y$=f/dy refers to a normalized focal length in a y-axis direction of the camera, both in a unit of pixel; f is a focal length of the camera, dx and dy respectively are physical sizes of the pixel in the x-axis and y-axis directions of the camera, and ($u_0$, $v_0$) are coordinates of an image center in a pixel coordinate system, in a unit of pixel.

$M_2$ is an extrinsic matrix.

A radial distortion equation is expressed by:

$$\hat{x}=x\left(1+k_1r^2+k_2r^4+k_3r^6\right)$$

$$\hat{y}=y\left(1+k_1r^2+k_2r^4+k_3r^6\right)$$

where, $k_1$ is a quadratic coefficient of the radial distortion, $k_2$ is a quartic coefficient of the radial distortion, and $k_3$ is a sextic coefficient of the radial distortion.

A tangential distortion equation is expressed by:

$$\hat{x}=x+2p_1xy+p_2\left(r^2+2x^2\right)$$

$$\hat{y}=y+p_1\left(r^2+2y^2\right)+2p_2xy$$

where, $P_1$ is a first tangential distortion coefficient, and $P_2$ is a second tangential distortion coefficient; (x,y) is an ideal undistorted image coordinates, ($\hat{x}$, $\hat{y}$) are a distorted image coordinates, and r is a distance from a point in an image to a center of the image, i.e., $r^2=x^2+y^2$.

The motion target detection and tracking device is configured to perform the distortion correction on the images captured by the cameras by using an undistort function in a computer vision library opencv, and the undistort function is expressed by:

void undistort(InputArray src, OutputArray dst, InputArray cameraMatrix, InputArray distCoeffs, InputArray newCameraMatrix)

where, src is a pixel matrix of an original image, and dst is a pixel matrix of a corrected image.

cameraMatrix is a camera intrinsic parameter:

$$cameraMatrix=\begin{bmatrix}f_x & 0 & u_0\\0 & f_y & v_0\\0 & 0 & 1\end{bmatrix}$$

where, $f_x$=f/dx refers to a normalized focal length in a x-axis direction of a camera, and $f_y$=f/dy refers to a normalized focal length in a y-axis direction of the camera, both in a unit of pixel; f is a focal length of the camera, dx and dy respectively are physical sizes of the pixel in the x-axis and y-axis directions of the camera, and ($u_0$, $v_0$) are coordinates of an image center in a pixel coordinate system, in a unit of pixel.

distCoeffs are distortion parameters:

$$distCoeffs=[k_1, k_2, p_1, p_2, k_3].$$

where, $k_1$ is a quadratic coefficient of radial distortion, $k_2$ is a quartic coefficient of radial distortion, $k_3$ is a sextic coefficient of radial distortion, $p_1$ and $p_2$ respectively are a first tangential distortion parameter and a second tangential distortion parameter, and InputArray newCameraMatrix is an all-zero matrix.

Figure 4:
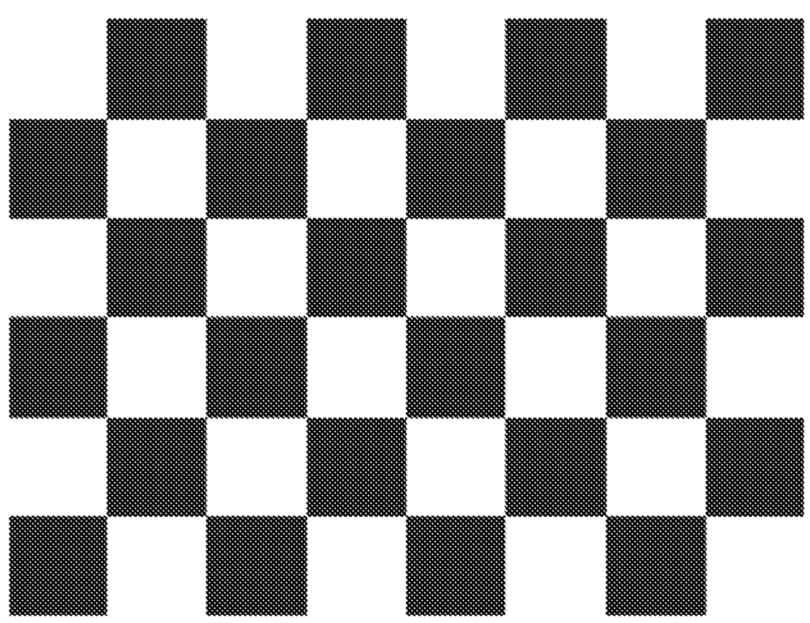
FIG. 4 is a checkerboard based on the Zhengyou Zhang calibration method according to an embodiment of the present disclosure.

The camera intrinsic parameter cameraMatrix and the distortion parameters distCoeffs are calibrated by:

preparing a checkerboard using the Zhengyou Zhang calibration method as a calibration board, and capturing the calibration board at different angles with the cameras to obtain a set of W checkerboard images, where 15≤W≤30, as shown in FIG. 4;

using a camera calibration tool Camera Calibration in a matlab toolbox to load the W checkerboard images, and automatically detecting an angular point in the checkerboard to obtain coordinates of the angular point in the pixel coordinate system;

inputting an actual cell size of the checkerboard into the calibration tool Camera Calibration, and calculating, by the calibration tool Camera Calibration, world coordinates of the angular point; and performing, by the calibration tool Camera Calibration, parameter solution based on the coordinates of the angular point in the W images in the pixel coordinate system and the coordinates of the angular point in the W images in the world coordinate system to obtain the camera intrinsic parameter cameraMatrix and the distortion parameters distCoeffs.

The motion target detection and tracking device is configured to call a perspectiveTransform function in a computer vision library opencv to convert the coordinates of the athlete in the pixel coordinate system into the coordinates in the world coordinate system of the coverage area of the field of view of the cameras.

The perspective projection matrix is acquired by steps S2.1 to S2.7 as follows.

In S2.1, the cameras are arranged and secured in the motion scene of the athlete, where the M cameras have the total field of view covering the whole motion scene of the athlete, and images of adjacent cameras are overlapped.

Figure 5:
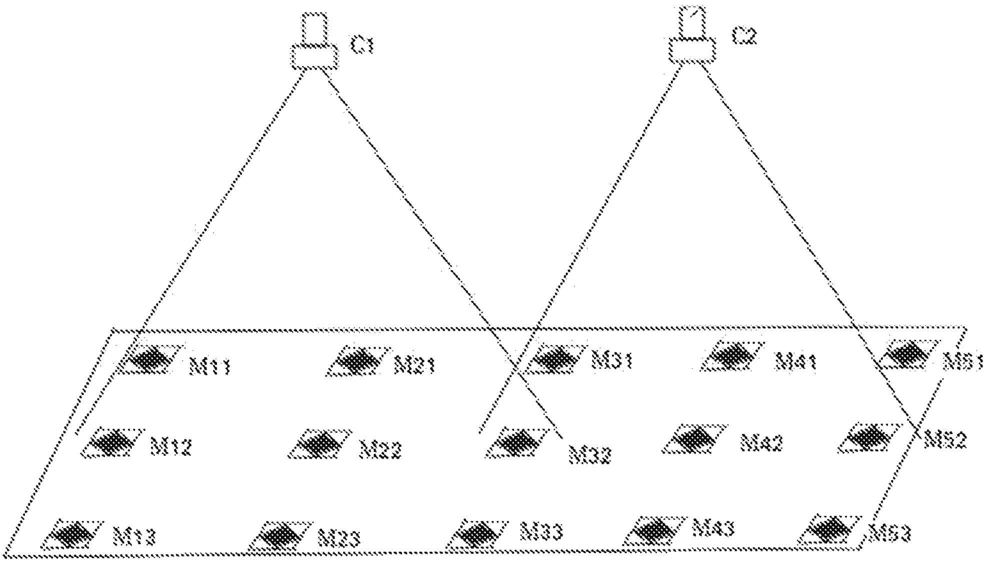
FIG. 5 is a schematic diagram of an arrangement of a calibration site for camera extrinsic parameters according to an embodiment of the present disclosure.

In S2.2, a field plane of the motion scene is defined as a XOY plane of the global world coordinate system, R rows and C columns of mark points are arranged on the field plane, where the rows of the mark points are parallel to a X-axis of the global world coordinate system, the columns of the mark points are parallel to a Y-axis of the global world coordinate system, each of the mark points is provided with a rhombus pattern, lines for connecting opposite vertices of the rhombus pattern are parallel to the X-axis and Y-axis of the global world coordinate system, and a position of a center point of a rhombus is determined as a position of the mark point; a field of view of each of the cameras contains $a^2$ mark points, which are evenly distributed in a form of a*a matrix, mark points located around are close to the edges of the field of view of the camera, and an overlapping area of fields of view of adjacent cameras contains a common mark points, as shown in FIG. 5. In an embodiment of the present disclosure, a is 3.

In S2.3, for each camera, a mark point in an upper left corner of the field of view of the camera is selected as an origin, i.e., has (0,0) as coordinates, an local world coordinate system of the field of view of the camera is established, and a position of each of the mark points relative to the origin is measured to obtain coordinates of nine mark points in the local world coordinate system of the field of view of the camera.

In S2.4, through camera capturing, an image containing $a^2$ mark points is obtained by the camera.

In S2.5, the distortion correction is performed on the image captured by the camera.

In S2.6, coordinates of $a^2$ mark points in the distorted and corrected image captured by the camera in the pixel coordinate system are determined.

The distorted and corrected image is displayed by matlab, a position of a point pointed by a mouse in the image is displayed by using an impixelinfo command, the mouse is pointed to a center of a rhombus mark to obtain positions of $a^2$ marks in the image, a center of the rhombus mark in an upper left corner of the image is defined as an origin of the pixel coordinate system, coordinates of which are recorded as (0,0), and positions of the remaining $a^2-1$ non-origin mark points relative to the origin are recoded as coordinates in the pixel coordinate system.

In S2.7. for the camera, the coordinates of the mark point in the pixel coordinate system and the corresponding coordinates in the local world coordinate system of the field of view of the camera are recorded as a set of coordinates, and $a^2$ sets of coordinates are inputted into a findHomography function in a computer vision library opencv to calculate the perspective projection matrix of the camera.

3.3 Motion Target Detection and Tracking Device 3.1 YOLO Model

The YOLO model is an object identification and location algorithm based on deep neural network, and the algorithm is as follows.

(1) A resolution of an image collected by a camera is converted to 416*416 and divided into S×S grid cells. In a specific embodiment of the present disclosure, S is seven.

(2) B bounding boxes (Bboxes) and confidence scores of the bounding boxes are predicted for each of the grid cells. In a specific embodiment of the present disclosure, B is two.

(3) Bounding box information is denoted by four values (x,y,w,h), where (x,y) are center coordinates of the bounding box, and w and h are the width and height of the bounding box, respectively.

(4) The confidence score includes two aspects. One is a possibility that the bounding box contains a target, and the other is accuracy of the bounding box. The former is denoted as Pr(object). In a case that the bounding box contains the target, Pr(object)=1; otherwise, Pr(object) =0 (containing only a background). The latter is characterized by an intersection over union (IOU) between a prediction box and a ground truth, which is denoted as $$IOU_{pred}^{truth}.$$

Thus, the confidence score is defined as $$c = Pr(\text{object}) * IOU_{pred}^{truth}.$$

(5) In addition to the bounding box, C category probability values are predicted for each of the grid cells, which is a probability that a target of a bounding box predicted by a cell belongs to each category, which is recorded as Pr(class|object).

Based on the description above, each of the grid cells is required to predict (B*5+C) values. It is assumed that B=2 and C=20, numerical values contained in the grid cell are shown in FIG. 2.

In a case that an input image is divided into S*S grid cells, a final prediction value is S*S*(B*5+C).

In an actual test, it is also required to calculate class-specific confidence scores of each bounding box:

$$Pr(class_i \mid \text{object}) * Pr(\text{object}) * \text{IOU}_{pred}^{truth} = Pr(class_i) * IOU_{pred}^{truth}.$$

where, for C categories, i=1, 2, . . . , C.

After obtaining class-specific confidence scores of each bounding box, a threshold is set (in this embodiment, the threshold is 0.5), a bounding box with a low score is filtered, and one or more reserved bounding boxes are subjected to non-maximum suppression algorithm (NMS) processing to obtain a final detection result. For each detected target, a final output contains seven values: four position values (x,y,w,h) (i.e., a final bounding box), one bounding box confidence score, one class-specific confidence score and one category code.

Figure 6:
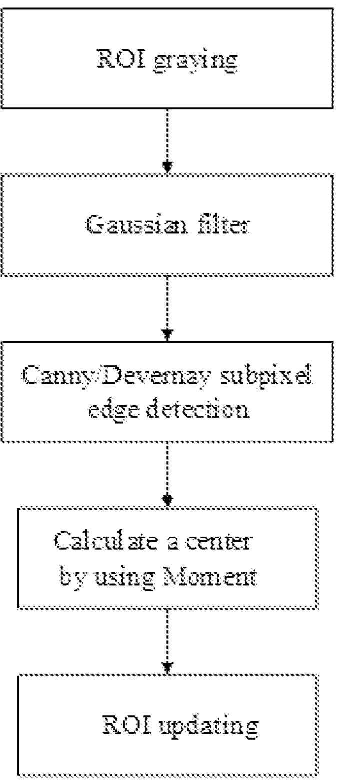
FIG. 6 is an edge detection flow according to an embodiment of the present disclosure.

The edge detection may process an image in a pixel level to precisely locate a target in the pixel level. A processing flow is shown in FIG. 6. The motion target detection and tracking device is configured to perform edge detection and other processing on a region of interest (ROI) of the bounding box detected by YOLO to obtain the precise position and the precise bounding box of each athlete in the pixel coordinate system through the following steps S3.1 to S3.5.

In S3.1, a ROI of the rough bounding box of each athlete detected by the YOLO, is subjected to graying and Gaussian filtering processing.

In S3.2, the ROI of the rough bounding box of the athlete is subjected to edge detection by using a Canny-Devernay algorithm, to obtain a precise contour of the athlete and a set of coordinates of contour points of the athlete.

In S3.3, moments of the contour are calculated based on the coordinates of the contour points of the athlete.

In S3.4, a center $(\bar{x}, \bar{y})$ of the athlete, i.e., the precise position of the athlete in the pixel coordinate system, is calculated by using the moments of the contour.

In an embodiment, an object cv:: Moments is obtained by using an opencv function cv:: moments, from which a zero-order moment $m_{00}$: and first-order moments $m_{10}$ and $m_{01}$ are obtained:

$$\bar{x} = \frac{m_{10}}{m_{00}}$$
$$\bar{y} = \frac{m_{01}}{m_{00}}.$$

In S3.5, a minimal circumscribed rectangle of a target contour is determined as a precise bounding box of the athlete.

The motion target detection and tracking device is configured to track the precise bounding boxes of all athletes at different instants by using a DeepSORT method.

The DeepSORT algorithm is an extension of a SORT algorithm. The SORT algorithm is an algorithm to achieve multi-target tracking, and its calculation process is as follows.

Before tracking, all athletes have been detected by a target detection algorithm.

In a case that a first frame image comes in, initialization is performed with a detected target Bbox, and a new tracker is established, marked with id.

For the subsequent frame comes in, a state prediction and a covariance prediction generated by a previous frame Bbox are obtained from the Kalman Filter first. Then, IOUs of all target states of the tracker and a Bbox detected in this frame are resolved; a unique match (data association part) with the maximum IOU is obtained by a Hungarian Algorithm, and matching pairs with matching values less than iou_threshold (generally 0.3) are removed.

The Kalman tracker is updated with a target detection Bbox matched in this frame, to update a state and a covariance, and output a state update value as a tracking Bbox of this frame. The tracker is reinitialized for a target that is not matched in this frame. Afterwards, the Kalman tracker performs a next round prediction.

The DeepSORT algorithm has not changed greatly in terms of an overall framework of SORT, which adds cascade matching and target confirmation, to enhance the effectiveness of tracking.

For a position sequence of the athlete in the global world coordinate system, a method of averaging by sets is used for filtering, and then a motion speed of a target is obtained by a differential operation on the average.

Figure 7:
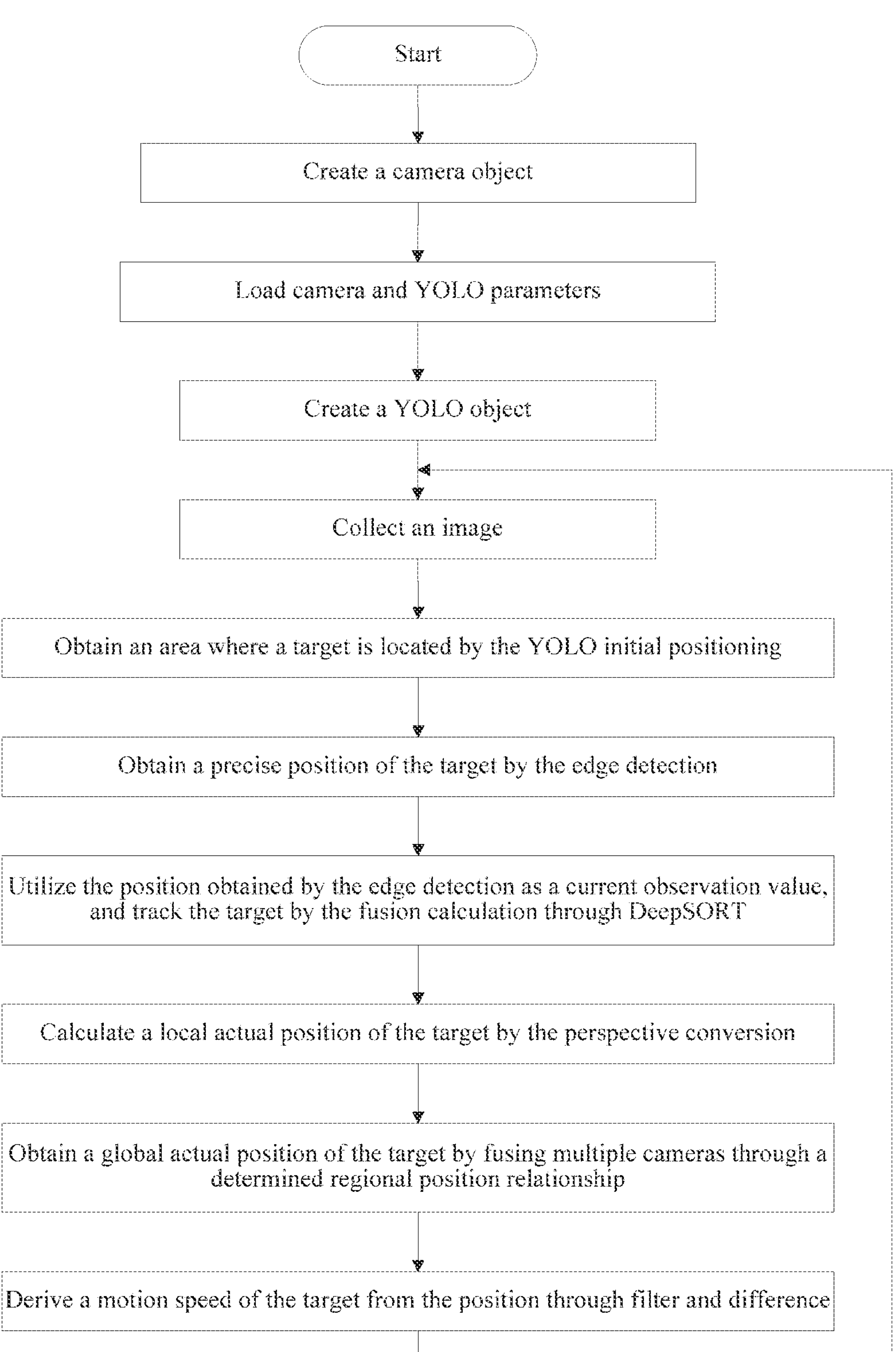
FIG. 7 is a flowchart of a target detection and tracking algorithm according to an embodiment of the present disclosure.

FIG. 7 is a general flow of target identification and tracking according to a specific embodiment of the present disclosure.

In a case that it is used in the field of swimming, a speed and a position of a swimmer may be tracked by identifying a color logo on a swimming cap as a target.

According to the present disclosure, multiple athletes may be identified at the same time, to calculate speeds and positions.

3.4 Motion Parameter Analysis Device

The motion parameter analysis device is configured to analyze the relative position and the attitude of the limb of the athlete in the body coordinate system of the athlete to obtain a motion joint angle, a step size of the athlete and a step frequency; compare positions and speeds of athletes in the world coordinate system of the motion scene to obtain a ranking of the athletes; and analyze and compare a difference between the motion parameters of the athlete and standard motion parameters to give improved training methods and guide the athletes to improve their training level.

For swimming, motion parameters such as the number of breaths, stroke frequency, stroke width, stroke times and turn time of different swimming strokes may further be obtained through conversion.

Due to a huge calculation amount of the data comprehensive analysis device, in a specific embodiment of the present disclosure, the data comprehensive analysis device is implemented by setting up a high-performance server, which, in an embodiment, includes a cloud computing server, a cloud storage server and a service management server.

The cloud computing server supports a second-generation intelligent Intel Xeon scalable processor, and supports 8 Tesla GPU acceleration cards in 2U space, which is a server with a highest GPU density per unit space at present. A GPU card with SXM2 and PCIe interfaces, and NVIDIA® NVLink2.0 high-speed interconnection technology are supported to achieve an aggregate bandwidth of 300 GB/s between GPUs. Hybrid CubeMesh interconnection improves a delay of multi-GPU data sharing, provides better acceleration ratio for computing, reduces system delay, and has strong overall performance. The cloud computing server is significantly applicable to deep learning model training, offline reasoning, scientific computing, engineering computing and research and other fields. The cloud computing server is used to implement all functions of the data comprehensive analysis device, which mainly includes the inertial navigation solution device, the motion target detection and tracking device, the motion target speed identification device and the motion parameter analysis device.

The storage server is a network storage product oriented for data storage requirements. Unified IP SAN and NAS features are provided to flexibly deploy a system architecture. A Snapshot Copy function is provided under an iSCSI configuration. A single machine may support up to 36 3.5-inch large-capacity hard disks. The system supports an expansion function of SAS JBOD, a mixed insertion of SAS and SATA disks, and 10 TB large-capacity hard disks; and supports automatic power supply failover and online replacement of faulty power supply, which can protect device cache data. A storage system and data are independent of each other and do not occupy data storage space. A special storage operating system is used to ensure performance and reliability of system access. A visual Chinese management interface is more convenient and easy to use. A user may configure disks and Raid sets and monitor their status on a GUI management interface. The storage server is configured to store all raw data collected by the data comprehensive analysis device and sent by the inertial navigation wearable devices and the cameras, and the position and the speed of the athlete in the world coordinate system of the motion scene as well as the relative position and the attitude of the limb of the athlete in the body coordinate system of the athlete calculated by itself and the like, to determine the motion parameters of the athlete. Based on information of the athlete and time, the information is stored for viewing and analysis.

The service management server mainly performs an interactive function with the terminal and the inertial navigation wearable devices, to synchronize data between the inertial navigation system and the cameras, and synchronize data between different inertial navigation wearable devices.

The service management server supports a new-generation Intel Xeon processor and up to 24 DIMM, which significantly improves application performance, and computing performance may be elevated by up to 70%.

4. Terminal

In a specific embodiment of the present disclosure, the terminal may be a PC, a tablet computer, or a mobile phone.

In addition to the above display function, based on a user requirement, the terminal is configured to support four types of identity users to use, i.e., an athlete, a coach, an expert and an administrator respectively.

A terminal with an athlete permission includes an autonomous training device, a viewing history data device and a first group communication device. After logging in to an application as the athlete, basic settings of "Training Mode", "Viewing History Data", "Group Communication" and "My Application" may be performed. The autonomous training device is configured to acquire real-time motion parameters from the data comprehensive analysis device and record the real-time motion parameters. The viewing history data device is configured to retrieve, based on a motion period and the basic information of the athlete, original images, motion parameters and a corresponding training evaluation of the period from the data comprehensive analysis device, to objectively find the shortcomings in personal training, and perform targeted training adjustments with the help of the expert and the coach to achieve improvements. The first group communication device is configured to receive a message from the athlete for mutual communication with the coach and the expert, share relevant data and achieve further improvements.

A terminal with a coach permission includes an athlete management device, a competition management device and a second group communication device. After logging in to an application as the coach, basic settings of "Athlete Management", "Competition Management", "Group Communication" and "My Application" may be performed. The athlete management device is configured to add or remove an athlete, and update basic information of the athlete in the data comprehensive analysis device. The viewing history data device is configured to retrieve, based on an externally inputted motion period and the basic information of the athlete, original images and motion parameters of the period from the data comprehensive analysis device, provide a training evaluation, and send the training evaluation to the data comprehensive analysis device for storage. The competition management device is configured to create a new intra-team contest, and send an intra-team contest grouping and a contest rule to the data comprehensive analysis device for storage, to invite the coach, the athlete, the expert and other personnel to participate together. The second group communication device is configured to receive a message from the coach for mutual communication with the athlete and the expert.

A terminal with an expert permission includes a training management device and a third group communication device. After logging in as the expert, basic settings of "Training Management", "Group Communication" and "My application" may be performed. The training management device is configured to view a ranking of training, compare motion parameters of athletes in a same game, evaluate and advise on the athletes and the training in the game, generate a data analysis report and send the data analysis report to the data comprehensive analysis device for storage. The third group communication device is configured to receive a message from the expert for mutual communication with the coach and the athlete, check data shared by the athlete, perform one-to-one accurate analysis and provide personalized assistant.

A terminal with an administrator identity, after logging in as the administrator, simple work processing may be performed on a mobile terminal, such as user information reset, user identity authorization, training data management and consultation message reply, etc.

In a specific implementation of the present disclosure, all data set by the terminal is stored in the data comprehensive analysis device.

Based on the above description, according to the present disclosure, quantitative analysis and control of various motion parameters of athletes are implemented through the inertial navigation wearable device, data comprehensive analysis device and the like, and an interactive communication between an athlete and a coach is implemented through real-time data, which provides a supporting means for better integration of standardization and personalization of training parameters.

Described above are only preferred embodiments of the present disclosure, and the protection scope of the present disclosure is not limited thereto. All changes or replacements that may be easily made by those skilled in the art within the technical scope disclosed in the present disclosure should fall within the protection scope of the present disclosure.

The content that is not described in detail in the specification of the present disclosure is deemed as common technologies to those skilled in the art.

The invention claimed is:

1. A system for intelligent measurement and digital training of human motion, comprising N inertial navigation wearable devices, M cameras, a data comprehensive analysis device and a terminal, wherein both N and M are greater than or equal to 1; wherein, a total field of view of the M cameras is configured to cover a motion scene of an athlete, and each camera is configured to capture an image in the field of view to form an image data frame and send the image data frame to the data comprehensive analysis device;

each inertial navigation wearable device is secured on a limb of the athlete in a wearable manner, and each inertial navigation wearable device is configured to measure a three-axis linear acceleration of the limb of the athlete and a three-axis angular velocity of the limb of the athlete in an inertial coordinate system by taking the limb of the athlete as a carrier, and send the three-axis linear acceleration and the three-axis angular velocity to a data comprehensive analysis device; and the data comprehensive analysis device is configured to store basic information of the athlete, and establish and maintain an association relationship between the athlete and an inertial navigation wearable device the athlete wears; perform, based on the three-axis linear acceleration of the limb of the athlete and the three-axis angular velocity of the limb of the athlete in the inertial coordinate system, navigation solution and coordinate conversion to obtain and store a relative position and an attitude of the limb of the athlete in a body coordinate system of the athlete; collect and store the image captured by a respective camera, and perform target identification, tracking and coordinate conversion on the image captured by the respective camera to obtain and store a position and a speed of the athlete in a world coordinate system of the motion scene; and analyze the position and the speed of the athlete in the world coordinate system of the motion scene as well as the relative position and the attitude of the limb of the athlete in the body coordinate system of the athlete to determine and store motion parameters of the athlete, wherein the data comprehensive analysis device comprises an inertial navigation solution device, a motion target detection and tracking device, a motion target speed identification device and a motion parameter analysis device;

the inertial navigation solution device is configured to perform, based on the three-axis linear acceleration of the limb of the athlete and the three-axis angular velocity of the limb of the athlete in the inertial coordinate system, the navigation solution to obtain attitude, speed and position information of the limb of the athlete in a navigation coordinate system; perform zero-velocity detection on motion of the limb of the athlete; and perform, in a case that the limb of the athlete is within a zero-velocity interval, zero-velocity error correction on the attitude, speed and position information of the limb of the athlete in the navigation coordinate system; and define the body coordinate system of the athlete, to convert the attitude, speed and position information of the limb of the athlete in the navigation coordinate system into corresponding information in the body coordinate system of the athlete;

the motion target detection and tracking device is configured to collect the image captured by the respective camera, record time for collecting the image, perform distortion correction on the image captured by the respective camera; perform target detection on each corrected image captured at a same time by using a you only look once YOLO model to obtain rough bounding boxes of all athletes in the image in a pixel coordinate system; obtain precise positions and precise bounding boxes of all athletes in the pixel coordinate system based on an edge detection method; and match precise bounding boxes of a respective athlete at different instants to track the precise bounding boxes of the respective athlete at different instants; convert coordinates of the respective athlete in the pixel coordinate system into coordinates in the world coordinate system corresponding to a coverage area of the field of view of the camera through a perspective projection matrix; calculate coordinates of the respective athlete in a global world coordinate system of the motion scene at different instants based on a position relationship among the coverage area of the field of view of the camera; and send the calculated coordinates to the motion target speed identification device;

the motion target speed identification device is configured to filter and denoise a coordinate sequence of the respective athlete in the global world coordinate system of the motion scene at different instants, and perform differential processing on the filtered and denoised coordinate sequence to obtain the speed of the athlete in the world coordinate system of the motion scene; and the motion parameter analysis device is configured to analyze the relative position and the attitude of the limb of the athlete in the body coordinate system of the athlete to obtain the motion parameters; compare positions and speeds of athletes in the world coordinate system of the motion scene, analyze and sort these data, and rank the athletes based on a determined rule; and perform contrast and comparison based on the motion parameters of the athlete and standard parameters.

2. The system for intelligent measurement and digital training of human motion according to claim 1, wherein the N inertial navigation wearable devices are worn on different limb parts of at least one athlete, and data outputted by the N inertial navigation wearable devices are synchronous.

3. The system for intelligent measurement and digital training of human motion according to claim 1, further comprising the terminal, wherein the terminal is configured to establish a three-dimensional model of the motion scene and a three-dimensional model of the athlete, associate a speed and a position of the athlete in a motion scene coordinate system as well as the relative position and the attitude of the limb of the athlete in the body coordinate system of the athlete with corresponding three-dimensional models, and display a motion process and the motion parameters of the athlete in a visualized manner.

4. The system for intelligent measurement and digital training of human motion according to claim 1, wherein the terminal is configured to support four types of identity users to use, comprising the athlete, a coach, an expert and an administrator;

in a case that the terminal is configured with an athlete permission, the terminal comprises an autonomous training device, a viewing history data device and a first group communication device, wherein the autonomous training device is configured to acquire real-time motion parameters from the data comprehensive analysis device and record the real-time motion parameters; the viewing history data device is configured to retrieve, based on a motion period and the basic information of the athlete, original images, motion parameters and a corresponding training evaluation of the motion period from the data comprehensive analysis device; and the first group communication device is configured to receive a message from the athlete for mutual communication with the coach and the expert;

in a case that the terminal is configured with an coach permission, the terminal comprises an athlete management device, a competition management device and a second group communication device, wherein the athlete management device is configured to add or remove an athlete, and update the basic information of the athlete in the data comprehensive analysis device; the viewing history data device is further configured to retrieve, based on an externally inputted motion period and the basic information of the athlete, original images and motion parameters of the motion period from the data comprehensive analysis device, provide a training evaluation, and send the training evaluation to the data comprehensive analysis device for storage; the competition management device is configured to create a new intra-team contest, and send an intra-team contest grouping and a contest rule to the data comprehensive analysis device for storage; and the second group communication device is configured to receive a message from the coach for mutual communication with the athlete and the expert;

in a case that the terminal is configured with an expert permission, the terminal comprises a training management device and a third group communication device, wherein the training management device is configured to view a ranking of training, compare motion parameters of athletes in a same game, evaluate and advise on the athletes and the training in the game, generate a data analysis report and send the data analysis report to the data comprehensive analysis device for storage; and the third group communication device is configured to receive a message from the expert for mutual communication with the coach and the athlete; and in a case that the terminal is configured with an administrator identity, the terminal is configured to set user information and a user identity.

5. The system for intelligent measurement and digital training of human motion according to claim 1, wherein the inertial navigation wearable device comprises an MEMS sensor, a signal processing device, a communication device and a lithium battery;

the MEMS sensor is internally integrated with an MEMS gyroscope and an MEMS accelerometer, wherein the MEMS gyroscope is configured to output the three-axis angular velocity in the inertial coordinate system, and the MEMS accelerometer is configured to output the three-axis linear acceleration of the limb of the athlete, and the MEMS sensor is configured to output a measurement result to the signal processing device;

the signal processing device is configured to frame and package the measurement result outputted by the MEMS sensor and send the framed and packaged measurement result to the communication device;

the communication device is configured to send a packaged measurement data frame by wireless communication; and the lithium battery is configured to supply power for the MEMS sensor, the signal processing device and the communication device.

6. The system for intelligent measurement and digital training of human motion according to claim 1, wherein the inertial navigation solution device is implemented by:

step S1, selecting an "east-north-up" geographical coordinate system as the navigation coordinate system, acquiring the three-axis linear acceleration of the limb of the athlete and the three-axis angular velocity of the limb of the athlete in the inertial coordinate system, and performing the navigation solution to obtain the attitude, speed and position information of the limb of the athlete in the navigation coordinate system;

step S2, establishing a Kalman filter by determining an attitude angle error, a speed error and a position error of the limb of the athlete in the navigation coordinate system, gyro zero bias and accelerometer zero bias in the MEMS sensor as state variables and determining a speed error and an attitude error of the limb of the athlete in the zero-velocity interval as measurements;

step S3, performing, at each sampling instant of the MEMS sensor, one-step prediction of the state variables of the Kalman filter, calculating a state one-step prediction error covariance matrix, and proceeding to step S4;

step S4, determining whether the limb of the athlete is within the zero-velocity interval, in a case that the limb of the athlete is within the zero-velocity interval, proceeding to step S5; in a case that the limb of the athlete is not within the zero-velocity interval, proceeding to step S6;

S5, updating the measurements and a measurement matrix of the Kalman filter, calculating a filtering gain and updating a state estimate error covariance matrix, based on the measurements, the state one-step prediction error covariance matrix, the state estimate error covariance matrix and a measurement noise covariance matrix, performing state estimate by the filtering gain and the measurement matrix to obtain the speed error, the position error and the attitude angle error of the limb of the athlete in the navigation coordinate system, and correcting the attitude, speed and position information of the limb of the athlete in the navigation coordinate system based on the estimated errors; and step S6, outputting the attitude, speed and position information of the limb of the athlete in the navigation coordinate system.

7. The system for intelligent measurement and digital training of human motion according to claim 6, wherein, in the step S1, the attitude of the limb of the athlete in the navigation coordinate system is calculated by:

step S1.1, acquiring the three-axis angular velocity $$\omega_{ib}^{b}$$

of the limb of the athlete in the inertial coordinate system;

step S1.2, calculating a three-axis angular velocity $$\omega_{nb}^{b}$$

of the limb of the athlete in the navigation coordinate system, based on the three-axis angular velocity $$\omega_{ib}^{b}$$

of the limb of the athlete in the inertial coordinate system;

step S1.3, calculating an attitude quaternion $Q_k$ of the limb of the athlete at a current sampling instant:

$$Q_k = \frac{1}{2}\begin{bmatrix} 2 & -\omega_{nbx}^{b}\times\Delta t & -\omega_{nby}^{b}\times\Delta t & -\omega_{nbz}^{b}\times\Delta t \\ \omega_{nbx}^{b}\times\Delta t & 2 & \omega_{nbz}^{b}\times\Delta t & -\omega_{nby}^{b}\times\Delta t \\ \omega_{nby}^{b}\times\Delta t & -\omega_{nbx}^{b}\times\Delta t & 2 & \omega_{nbx}^{b}\times\Delta t \\ \omega_{nbz}^{b}\times\Delta t & \omega_{nby}^{b}\times\Delta t & -\omega_{nbx}^{b}\times\Delta t & 2 \end{bmatrix} Q_{k-1}$$

wherein Δt is a sampling interval of the MEMS sensor, and $Q_{k-1}$ is an attitude quaternion of the limb of the athlete at a previous sampling instant;

step S1.4, calculating a coordinate conversion matrix $$C_b^n$$

from the body coordinate system of the limb of the athlete to the navigation coordinate system, based on the attitude quaternion $Q_k$ of the limb of the athlete at the current sampling instant; and step S1.5, calculating the attitude of the limb of the athlete in the navigation coordinate system, based on the coordinate conversion matrix $$C_b^n$$

from the body coordinate system of the limb of the athlete to the navigation coordinate system, wherein the attitude of the limb of the athlete in the navigation coordinate system comprises a pitch angle θ, a roll angle γ and a yaw angle ψ of the limb of the athlete; and the calculating the attitude of the limb of the athlete in the navigation coordinate system further comprises:

$$\text{based on } (C_b^n)^T = \begin{bmatrix} T_{11} & T_{12} & T_{13} \\ T_{21} & T_{22} & T_{23} \\ T_{31} & T_{32} & T_{33} \end{bmatrix}, \text{ deriving } \begin{matrix} \theta = \arcsin(T_{32}) \\ \gamma = \arctan\left(-\frac{T_{31}}{T_{33}}\right) \\ \psi = rc\tan\left(\frac{T_{12}}{T_{22}}\right) \end{matrix}.$$

8. The system for intelligent measurement and digital training of human motion according to claim 6, wherein, in the step S1, the speed of the limb of the athlete in the navigation coordinate system is calculated by:

step S1.6, substituting a coordinate conversion matrix $$C_b^n$$

from the body coordinate system of the limb of the athlete to the navigation coordinate system into a specific force equation to obtain a projection $$\dot{V}_{en}^{n}$$

of an acceleration of the navigation coordinate system relative to Earth coordinate system in the navigation coordinate system;

the specific force equation is $$\dot{V}_{en}^{n} = C_{b}^{n} \times f^{b} - (2\omega_{ie}^{n} + \omega_{en}^{n}) \times V_{en}^{n} + g^{n}$$

wherein $f^b$ is the three-axis linear acceleration of the limb of the athlete in the inertial coordinate system, $$\omega_{ie}^{n}$$

is a projection of an angular velocity of the Earth coordinate system relative to the inertial coordinate system in the navigation coordinate system, $$\omega_{en}^{n}$$

is a projection of an angular velocity of the navigation coordinate system relative to the Earth coordinate system in the navigation coordinate system, and $g^n$ is a projection of a gravity acceleration in the navigation coordinate system; and step S1.7, updating, based on equation $$V_{en,k}^{n} = V_{en,k-1}^{n} + \dot{V}_{en}^{n} \cdot \Delta t,$$

a projection of a speed of the navigation coordinate system relative to the Earth coordinate system in the navigation coordinate system, which is the speed of the limb of the athlete in the navigation coordinate system, wherein $$V_{en,k-1}^{n}$$

is a projection of a speed of the navigation coordinate system relative to the Earth coordinate system in the navigation coordinate system at a previous sampling instant, and $$V_{en,k}^{n}$$

is a projection of a speed of the navigation coordinate system relative to the Earth coordinate system in the navigation coordinate system at a current sampling instant.

9. The system for intelligent measurement and digital training of human motion according to claim 6, wherein the position information of the limb of the athlete in the navigation coordinate system in the step S1 is updated, based on an equation $$P_k = P_{k-1} + V_{en,k-1}^{n} \cdot \Delta t,$$

wherein Δt is a sampling interval of the MEMS sensor, $P_{k-1}$ is a position at a previous sampling instant, $P_k$ is a position at a current sampling instant, and $$V_{en,k-1}^{n}$$

is a projection of a speed of the navigation coordinate system relative to the Earth coordinate system in the navigation coordinate system at the previous sampling instant.

10. The system for intelligent measurement and digital training of human motion according to claim 6, wherein determining whether a speed of the limb of the athlete is within the zero-velocity interval comprises:

sending raw data outputted by an MEMS gyroscope and an MEMS accelerometer to a zero-velocity detector, and calculating, by the zero-velocity detector, statistical magnitude of motion energy of the limb of the athlete, setting a threshold of the zero-velocity detector; determining that the limb of the athlete is within the zero-velocity interval, in a case that the statistical magnitude of the zero-velocity detector is lower than a preset threshold of the zero-velocity detector; determining that the limb of the athlete is outside the zero-velocity interval, in a case that the statistical magnitude of the zero-velocity detector is not lower than the preset threshold of the zero-velocity detector.

11. The system for intelligent measurement and digital training of human motion according to claim 10, wherein, for different limbs of the athlete, calculating, by the zero-velocity detector, energy statistical values of motions of the limbs of the athlete with different algorithms, comprising: in a case that the limbs of the athlete are human feet, calculating, by the zero-velocity detector, the energy statistical values with a GLRT or ARE algorithm; and in a case that the limbs of the athlete are human thighs or calves, calculating, by the zero-velocity detector, the energy statistical values with a MAG or MV algorithm.

12. The system for intelligent measurement and digital training of human motion according to claim 6, wherein the state variables X in the Kalman filter in the step S2 are:

$$X = [\varphi_x \ \varphi_y \ \varphi_z \ \delta v_x \ \delta v_y \ \delta v_z \ \delta x \ \delta y \ \delta z \ \varepsilon_{bx} \ \varepsilon_{by} \ \varepsilon_{bz} \ \nabla_{bx} \ \nabla_{by} \ \nabla_{bz}],$$

wherein $\varphi_x$ $\varphi_y$ $\varphi_z$ are the attitude angle errors of the limb of the athlete in the navigation coordinate system, $\delta v_x$ $\delta v_y$ $\delta v_z$ are the speed errors of the limb of the athlete in the navigation coordinate system, δx δy δz are the position errors of the limb of the athlete in the navigation coordinate system, $\varepsilon_{bx}$ $\varepsilon_{by}$ $\varepsilon_{bz}$ are the gyro zero biases, and $\nabla_{bx}$ $\nabla_{by}$ $\nabla_{bz}$ are the accelerometer zero biases;

a state equation is expressed by:

$$X_k = \Phi_{k/k-1} X_{k-1} + \Gamma_{k-1} W_{k-1},$$

wherein X is a state variable, $\Phi$ is a one-step transition matrix, $\Gamma$ is a process noise distribution matrix, W is a process noise matrix, k−1 and k respectively are a (k−1)-th sampling instant and a k-th sampling instant, and k/k−1 is a one-step prediction from the (k−1)-th sampling instant to the k-th sampling instant;

$$\Phi = \begin{bmatrix} F_{11} & F_{12} \\ O_{6\times 9} & O_{6\times 6} \end{bmatrix}_{15\times 15} \quad F_{11} = \begin{bmatrix} O_{3\times 3} & O_{3\times 3} & O_{3\times 3} \\ f^n\times & O_{3\times 3} & O_{3\times 3} \\ O_{3\times 3} & I_{3\times 3} & O_{3\times 3} \end{bmatrix} \quad F_{12} = \begin{bmatrix} -C_b^n & O_{3\times 3} \\ O_{3\times 3} & C_b^n \\ O_{3\times 3} & O_{3\times 3} \end{bmatrix}$$

$$W = [\, w_{gx} \;\; w_{gy} \;\; w_{gz} \;\; w_{ax} \;\; w_{ay} \;\; w_{az} \,]^T,$$

wherein W is the process noise matrix, $w_{gx}$, $w_{gy}$ and $w_{gz}$ respectively are noises of a three-axis gyroscope, $w_{ax}$, $w_{ay}$ and $w_{az}$ are noises of a three-axis accelerometer, $$(f^n\times) = \begin{bmatrix} 0 & -f_z^n & f_y^n \\ f_z^n & 0 & -f_x^n \\ -f_y^n & f_y^n & 0 \end{bmatrix}$$

is an antisymmetric matrix composed of $$f^n[f_x^n, f_y^n, f_z^n];$$

and $$f_x^n, f_y^n, f_z^n$$

is the three-axis linear acceleration of the carrier in the navigation coordinate system;

the process noise distribution matrix $\Gamma$ is $$\Gamma = \begin{bmatrix} -C_b^n & O_{3\times 3} \\ O_{3\times 3} & C_b^n \\ O_{9\times 3} & O_{9\times 3} \end{bmatrix}_{15\times 6};$$

the measurements are $$Z_k = \begin{bmatrix} V_x - 0 \\ V_y - 0 \\ V_z - 0 \\ \psi_{Z_k} - \psi_{Z_{k-1}} \end{bmatrix},$$

wherein $V_x$, $V_y$ and $V_z$ respectively are three-axis components of the speed of the limb of the athlete in the navigation coordinate system; and $\psi_{Z_k}$ and $\psi_{Z_{k-1}}$ respectively are attitude angle data of the limb of the athlete at a previous sampling instant and a current sampling instant; and measurement equations are:

$$Z_k = H_k X_k + U_k;$$

$$H = \begin{bmatrix} O_{3\times 3} & I_{3\times 3} & O_{3\times 3} & O_{3\times 3} & O_{3\times 3} \\ H_{21} & O_{1\times 3} & O_{1\times 3} & H_{24} & O_{1\times 3} \end{bmatrix};$$

-continued $$H_{21} = [\, 0 \;\; 0 \;\; -\omega_{ie} \;\; \tan\gamma \;\; \cos\psi \;\; \cos \;\; L\Delta t \,]$$

$$H_{24} = [\, 0 \;\; \sec\gamma \;\; \sin\theta \;\; \Delta t \;\; \sec\gamma \;\; \cos\theta \;\; L\Delta t \,]$$

$$U = [\, w_{\delta v_x} \;\; w_{\delta v_y} \;\; w_{\delta v_z} \;\; w_{\delta \psi_z} \,]^T,$$

wherein $\omega_{ie}$ is an angular velocity of Earth rotation, L is a latitude of Earth where the carrier is located, U is a measurement noise matrix; $W_{\delta v_x}$, $W_{\delta v_y}$ and $W_{\delta v_z}$ respectively are three-axis velocity error noises, $W_{\delta \psi_z}$, is an attitude angle error noise, $\theta$, $\gamma$ and $\psi$ respectively are a pitch angle, a roll angle and a yaw angle of the limb of the athlete, and $\Delta t$ is a sampling interval of the MEMS sensor.

13. The system for intelligent measurement and digital training of human motion according to claim 1, wherein the motion target detection and tracking device is configured to perform the distortion correction on the image captured by the respective camera by using an undistort function in a computer vision library opencv, and the undistort function is expressed by:

void undistort (InputArray src, OutputArray dst, InputArray cameraMatrix, InputArray distCoeffs, InputArray newCameraMatrix), wherein, src is a pixel matrix of an original image, and dst is a pixel matrix of a corrected image;

cameraMatrix is a camera intrinsic parameter:

$$cameraMatrix = \begin{bmatrix} f_x & 0 & u_0 \\ 0 & f_y & v_0 \\ 0 & 0 & 1 \end{bmatrix},$$

wherein $F_x$=f/dx refers to a normalized focal length in a x-axis direction of the respective camera, and $f_y$=f/dy refers to a normalized focal length in a y-axis direction of the respective camera, both in a unit of pixel; f is a focal length of the respective camera, dx and dy respectively are physical sizes of the pixel in the x-axis and y-axis directions of the respective camera, and $(u_0, v_0)$ are coordinates of an image center in the pixel coordinate system, in a unit of pixel;

distCoeffs are distortion parameters:

$$distCoeffs = [\, k_1, \;\; k_2, \;\; p_1, \;\; p_2, \;\; k_3 \,],$$

wherein $k_1$ is a quadratic coefficient of radial distortion,: $k_2$ is a quartic coefficient of radial distortion, $k_3$ is a sextic coefficient of radial distortion, $p_1$ and $p_2$ respectively are a first tangential distortion parameter and a second tangential distortion parameter, and InputArray newCameraMatrix is an all-zero matrix.

14. The system for intelligent measurement and digital training of human motion according to claim 13, wherein the camera intrinsic parameter cameraMatrix and the distortion parameters distCoeffs are calibrated by:

preparing a checkerboard using the Zhengyou Zhang calibration method as a calibration board, and capturing the calibration board at different angles with the camera to obtain a set of W checkerboard images, wherein 15≤W≤30;

using a camera calibration tool Camera Calibration in a matlab toolbox to load the W checkerboard images, and automatically detecting an angular point in the checkerboard to obtain coordinates of the angular point in the pixel coordinate system;

inputting an actual cell size of the checkerboard into the calibration tool Camera Calibration, and calculating, by the calibration tool Camera Calibration, world coordinates of the angular point; and performing, by the calibration tool Camera Calibration, parameter solution based on the coordinates of the angular point in the W images in the pixel coordinate system and the coordinates of the angular point in the W images in the world coordinate system to obtain the camera intrinsic parameter cameraMatrix and the distortion parameters distCoeffs.

15. The system for intelligent measurement and digital training of human motion according to claim 1, wherein the motion target detection and tracking device is configured to call a perspectiveTransform function in a computer vision library opencv to convert the coordinates of the athlete in the pixel coordinate system into the coordinates in the world coordinate system of the coverage area of the field of view of the camera.

16. The system for intelligent measurement and digital training of human motion according to claim 1, wherein M is greater than 1 and the perspective projection matrix is acquired by:

step S2.1, arranging and securing the cameras in the motion scene of the athlete, wherein the M cameras have the total field of view covering the motion scene of the athlete, and images of adjacent cameras are overlapped;

step S2.2, defining a field plane of the motion scene as a XOY plane of the global world coordinate system, arranging R rows and C columns of mark points on the field plane, wherein the rows of the mark points are parallel to a X-axis of the global world coordinate system, the columns of the mark points are parallel to a Y-axis of the global world coordinate system, each of the mark points is provided with a rhombus pattern, lines for connecting opposite vertices of the rhombus pattern are parallel to the X-axis and Y-axis of the global world coordinate system, and a position of a center point of a rhombus is determined as a position of the mark point; a field of view of each of the cameras contains $a^2$ mark points, which are evenly distributed in a form of a*a matrix, mark points located around are close to edges of the field of view of each camera, and an overlapping area of fields of view of adjacent cameras contains a common mark points;

step S2.3, for each camera, selecting a mark point in an upper left corner of the field of view of the camera as an origin with coordinates (0,0), establishing an local world coordinate system of the field of view of the camera, and measuring a position of each of the mark points relative to the origin to obtain coordinates of nine mark points in the local world coordinate system of the field of view of the camera;

step S2.4, through camera capturing, obtaining, by each camera, an image containing $a^2$mark points;

step S2.5, performing the distortion correction on the image captured by each camera;

step S2.6, determining coordinates of the $a^2$ mark points in the distorted and corrected image captured by each camera in the pixel coordinate system; and step S2.7, for each camera, recording the coordinates of each mark point in the pixel coordinate system and a corresponding coordinates in the local world coordinate system of the field of view of the camera as a set of coordinates, and transmitting $a^2$ sets of coordinates into a findHomography function in a computer vision library opencv to calculate the perspective projection matrix of the camera.

17. The system for intelligent measurement and digital training of human motion according to claim 16, wherein the determining coordinates of the $a^2$ mark points in the distorted and corrected image in the pixel coordinate system comprises:

displaying, by matlab, the distorted and corrected image, displaying a position of a point pointed by a mouse in the image by using an impixelinfo command, pointing the mouse to a center of a rhombus mark to obtain positions of $a^2$ marks in the image, defining a center of the rhombus mark in an upper left corner of the image as an origin of the pixel coordinate system with recorded coordinates (0,0), and recording positions of remaining $a^2$-1 non-origin mark points relative to the origin as coordinates in the pixel coordinate system.

18. The system for intelligent measurement and digital training of human motion according to claim 1, wherein the motion target detection and tracking device is configured to obtain the precise positions and the precise bounding boxes of all athletes in the pixel coordinate system by:

step S3.1, for each of the rough bounding boxes of all athletes detected by the YOLO, performing graying and Gaussian filtering processing on a Region Of Interest (ROI) of the rough bounding box;

step S3.2, performing edge detection on the ROI of the rough bounding box of the athlete by using a Canny-Devernay algorithm to obtain a precise contour of the athlete and a set of coordinates of contour points of the athlete;

step S3.3, calculating moments of the contour based on the coordinates of the contour points of the athlete;

step S3.4, calculating, by using the moments of the contour, a center $(\bar{x}, \bar{y})$ of the athlete, which is the precise position of the athlete in the pixel coordinate system; and step S3.5, determining a smallest circumscribed rectangle of a target contour as a precise bounding box of the athlete.

19. The system for intelligent measurement and digital training of human motion according to claim 1, wherein the motion target detection and tracking device is configured to track the precise bounding boxes of all motion targets at different instants by using a DeepSORT method.

* * * * *